United States Patent
Qasba et al.

(10) Patent No.: US 8,512,991 B2
(45) Date of Patent: Aug. 20, 2013

(54) BETA 1,4-GALACTOSYLTRANSFERASES WITH ALTERED DONOR AND ACCEPTOR SPECIFICITIES, COMPOSITIONS AND METHODS OF USE

(75) Inventors: Pradman K. Qasba, Bethesda, MD (US); Boopathy Ramakrishnan, Frederick, MD (US); Elizabeth Boeggeman, Bethesda, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 529 days.

(21) Appl. No.: 12/674,655

(22) PCT Filed: Aug. 22, 2007

(86) PCT No.: PCT/US2007/018656
§ 371 (c)(1),
(2), (4) Date: Feb. 22, 2010

(87) PCT Pub. No.: WO2009/025645
PCT Pub. Date: Feb. 26, 2009

(65) Prior Publication Data
US 2011/0064663 A1    Mar. 17, 2011

(51) Int. Cl.
*C12N 9/10*    (2006.01)
*C12P 19/24*    (2006.01)
(52) U.S. Cl.
USPC .......................................... 435/193; 435/94.5

(58) Field of Classification Search
None
See application file for complete search history.

(56) References Cited

FOREIGN PATENT DOCUMENTS
WO    2005/056783 A1    6/2005

OTHER PUBLICATIONS

Boeggeman, Elizabeth, et al: "Direct Identification of Nonreducing GlcNAc Residues on N-glycans of Glycoproteins Using a Novel Chemoenzymatic Method", Bioconjugate Chemistry, vol. 18, No. 3, May 2007, pp. 806-814.
Ramakrishnan, B., et al: "Structure-Based Design of Beta1, 4-galactosyltransferase I (beta4GalpT1) with Equally Efficient N-acetylgalactosaminyltransferase Activity. Point Mutation Broadens Beta4Gal-T1 Donor Specificity", Journal of Biological Chemistry, American Society of Biolochemical Biologists, Birmingham, US, vol. 277, No. 3, 7 Jun. 2002, pp. 20833-20839.

*Primary Examiner* — Tekchand Saidha
*Assistant Examiner* — Md. Younus Meah
(74) *Attorney, Agent, or Firm* — Edwards Wildman Palmer LLP; Peter F. Corless; Christine C. O'Day

(57) ABSTRACT

The invention relates generally to beta (1,4)-galactosyltransferase I mutants having altered donor and acceptor specificities, and methods of use thereof. In addition, the invention relates to methods for synthesizing oligosaccharides using the beta (1,4)-galactosyltransferase I mutants and to using the beta (1,4)-galactosyltransferase I mutants to conjugate agents, such as therapeutic agents or diagnostic agents, to acceptor molecules.

7 Claims, 10 Drawing Sheets

SEQ ID NO: 1

```
  1 CTGCCCGCAT GCCCTGAGGA GTCCCCGCTG CTTGTGGGCC CCATGCTGAT
 51 TGAGTTTAAC ATGCCTGTGG ACCTGGAGCT CGTGGCAAAG CAGAACCCAA
101 ATGTGAAGAT GGGCGGCCGC TATGCCCCCA GGGACTGCGT CTCTCCTCAC
151 AAGGTGGCCA TCATCATTCC ATTCCGCAAC CGGCAGGAGC ACCTCAAGTA
201 CTGGCTATAT TATTTGCACC CAGTCCTGCA GCGCCAGCAG CTGGACTATG
251 GCATCTATGT TATCAACCAG GCGGGAGACA CTATATTCAA TCGTGCTAAG
301 CTCCTCAATG TTGGCTTTCA AGAAGCCTTG AAGGACTATG ACTACACCTG
351 CTTTGTTGTT AGTGACGTGG ACCTCATTCC AATGAATGAC CATAATGCGT
401 ACAGGTGTTT TTCACAGCCA CGGCACATTT CCGTTGCAAT GGATAAGTTT
451 GGATTCAGCC TACCTTATGT TCAGTTGTTT GGAGGTGTCT CTGCTCTAAG
501 TAAACAACAG TTTCTAACCA TCAATGGATT TCCTAATAAT TATTGGGGCT
551 GGGGAGGAGA AGATGATGAC ATTTTTAACA GATTAGTTTT TAGAGGCATG
601 TCTATATCTC GCCCAAATGC TGTGGTCGGG AGGACGCGTC ACATCCGCCA
651 CTCGAGAGAC AAGAAAAATG AACCCAATCC TCAGAGGTTT GACCGAATTG
701 CACACACAAA GGAGACAATG CTCTCTAATG GTTTGAACTC ACTCACCTAC
751 CAGGTGCTGG ATGTACAGAG ATACCCATTG TATACCCCAAA TCACAGTGGA
801 CATCGGGACA CCGAGCTAG
```

SEQ ID NO: 2

127 LPACPEESPL LVGPMLIEFN MPVDLELVAK QNPNVKMGGR YAPRDCVSPH

177 KVAIIPFRN RQEHLKYWLY YLHPVLQRQQ LDYGIYVINQ AGDTIFNRAK

227 LLNVGFQEAL KDYDYTCFVF SDVDLIPMND HNAYRCFSQP RHISVAMDKF

277 GFSLPYVQLF GGVSALSKQQ FLTINGFPNN YWGWGGEDDD IFNRLVFRGM

327 SISRPNAVVG RTRHIRHSRD KKNEPNPQRF DRIAHTKETM LSNGLNSLTY

377 QVLDVQRYPL YTQITVDIGT PS*

Figure 4 (1/2)

SEQ ID NO: 3

```
Met Arg Leu Arg Glu Pro Leu Leu Ser Arg Ser Ala Ala Met Pro Gly
  1               5                  10                  15
Met Arg Phe Arg Glu Gln Phe Leu Gly Gly Ser Ala Ala Met Pro Gly
                 20                  25                  30
Ala Thr Leu Gln Arg Ala Ala Cys Arg Leu Val Ala Val Cys Ala Leu
                 35                  40                  45
His Leu Gly Val Thr Leu Val Tyr Tyr Leu Ser Gly Arg Asp Leu Ser
                 50                  55                  60
Arg Leu Pro Gln Leu Val Gly Val Ser Ser Thr Leu Gln Gly Gly Thr
 65                  70                  75                  80
Asn Gly Ala Ala Ala Ser Lys Gln Pro Gly Gln Pro Gly Gln Arg Pro Arg
                 85                  90                  95
Gly Ala Arg Pro Pro Pro Leu Gly Val Ser Pro Lys Pro Arg Pro
                 100                 105                 110
Gly Leu Asp Ser Ser Pro Gly Ala Ala Ser Gly Pro Gly Leu Lys Ser
 115                 120                 125
Asn Leu Ser Ser Leu Pro Val Pro Thr Thr Thr Gly Leu Leu Ser Leu
                 130                 135                 140
Pro Ala Cys Pro Glu Glu Ser Pro Leu Leu Val Gly Pro Met Leu Ile
                 145                 150                 155
Asp Phe Asn Ile Ala Val Asp Leu Leu Leu Ala Lys Lys Asn Pro
 160                 165                 170                 175
Glu Ile Lys Thr Gly Gly Arg Tyr Ser Pro Lys Asp Cys Val Ser Pro
```

Figure 4 (2/2)

SEQ ID NO: 3 (continued)

His Lys Val Ala Ile Ile Pro Phe Arg Asn Arg Gln Glu His Leu
180                     185                     190

Lys Tyr Trp Leu Tyr Tyr Leu His Pro Ile Leu Gln Arg Gln Gln Leu
195                     200                     205

Asp Tyr Gly Ile Tyr Val Ile Asn Gln Ala Gly Asp Thr Met Phe Ala
210                     215                     220

Arg Ala Lys Leu Leu Asn Ile Gly Phe Gln Glu Ala Leu Lys Asp Tyr
225                     230                     235                     240

Asp Tyr Asn Cys Phe Val Phe Ser Asp Val Asp Leu Ile Pro Met Asp
245                     250                     255

Asp Arg Asn Ala Tyr Arg Cys Phe Ser Gln Pro Arg His Ile Ser Val
260                     265                     270

Ala Met Asp Lys Phe Gly Phe Ser Leu Pro Tyr Val Gln Tyr Phe Gly
275                     280                     285

Gly Val Ser Ala Leu Ser Lys Gln Gln Phe Leu Ala Ile Asn Gly Phe
290                     295                     300

Pro Asn Asn Tyr Trp Gly Trp Gly Gly Glu Asp Asp Ile Phe Asn
305                     310                     315                     320

Arg Leu Val His Lys Gly Met Ser Ile Ser Arg Pro Asn Ala Val Val
325                     330                     335

Gly Arg Cys Arg Met Ile Arg His Ser Arg Asp Lys Lys Asn Glu Pro
340                     345                     350

Asn Pro Gln Arg Phe Asp Arg Ile Ala His Thr Lys Glu Thr Met Arg
355                     360                     365

Phe Asp Gly Leu Asn Ser Leu Thr Tyr Lys Val Leu Asp Val Gln Arg
370                     375                     380

Tyr Pro Leu Tyr Thr Gln Ile Thr Val Asp Ile Gly Thr Pro Arg
385                     390                     395

Figure 5 (1/2)
SEQ ID NO: 4

```
Met Lys Phe Arg Glu Pro Leu Leu Gly Gly Ser Ala Ala Met Pro Gly
  1               5                  10                  15

Ala Ser Leu Gln Arg Ala Cys Arg Leu Leu Val Ala Val Cys Ala Leu
         20                  25                  30

His Leu Gly Val Thr Leu Val Tyr Tyr Leu Ala Gly Arg Asp Leu Arg
         35                  40                  45

Arg Leu Pro Gln Leu Val Gly Val Ser Pro Leu Pro Gln Gly Ser Ser
 50                  55                  60

His Gly Ala Ala Ala Ile Gly Gln Pro Ser Gly Glu Leu Arg Leu Arg
 65                  70                  75                  80

Gly Val Ala Pro Pro Pro Leu Gln Asn Ser Ser Lys Pro Arg Arg Ser
         85                  90                  95

Arg Ala Pro Ser Asn Leu Asp Ala Tyr Ser His Pro Gly Pro Gly Pro
        100                 105                 110

Gly Pro Gly Ser Asn Leu Thr Ser Ala Pro Val Pro Ser Thr Thr Thr
    115                 120                 125

Arg Ser Leu Thr Ala Cys Pro Glu Glu Ser Pro Leu Leu Val Gly Pro
    130                 135                 140

Met Leu Ile Glu Phe Asn Ile Pro Val Asp Leu Lys Leu Ile Glu Gln
    145                 150                 155                 160

Gln Asn Pro Lys Val Lys Leu Gly Gly Arg Tyr Thr Pro Met Asp Cys
    165                 170                 175

Ile Ser Pro His Lys Val Ala Ile Ile Ile Pro Phe Arg Asn Arg Gln
    180                 185                 190

Glu His Leu Lys Tyr Trp Leu Tyr Tyr Leu His Pro Met Val Gln Arg
    195                 200                 205
```

Figure 5 (2/2)
SEQ ID NO: 4 (continued)

```
Gln Gln Leu Asp Tyr Gly Ile Tyr Val Ile Asn Gln Ala Gly Glu Ser
            210                 215                 220
Met Phe Asn Arg Ala Lys Leu Asn Val Gly Phe Lys Phe Gln Ala Leu
        225                 230                 235             240
Lys Asp Tyr Asp Tyr Asn Cys Phe Val Phe Ser Asp Val Asp Leu Ile
            245                 250                 255
Pro Met Asn Asp His Asn Thr Tyr Arg Cys Phe Ser Gln Pro Arg His
        260                 265                 270
Ile Ser Val Ala Met Asp Lys Phe Gly Phe Ser Leu Pro Tyr Val Gln
            275                 280                 285
Tyr Phe Gly Gly Val Ser Ala Leu Ser Lys Gln Gln Phe Leu Ser Ile
        290                 295                 300
Asn Gly Phe Pro Asn Asn Tyr Trp Gly Trp Gly Gly Glu Asp Asp Asp
            305                 310                 315                 320
Ile Tyr Asn Arg Leu Ala Phe Arg Gly Met Ser Val Ser Arg Pro Asn
        325                 330                 335
Ala Val Ile Gly Lys Cys Arg Met Ile Arg His Ser Arg Asp Lys Lys
            340                 345                 350
Asn Glu Pro Asn Pro Gln Arg Phe Asp Arg Ile Ala His Thr Lys Glu
        355                 360                 365
Thr Met Leu Ser Asp Gly Leu Asn Ser Leu Thr Tyr Met Val Leu Glu
    370                 375                 380
Val Gln Arg Tyr Pro Leu Tyr Thr Lys Ile Thr Val Asp Ile Gly Thr
        385                 390                 395                 400
Pro Ser
```

Figure 6

SEQ ID NO: 5

1 ttggcctggc ctgctgtctg ctggatctg aatgaccaaa ccacttccca ccatgctgcc 61 tggaaggact aaatgaagtc atgagtataa agtgctcctg catggccagc agccggatgc
121 ccgggcccac tgggcgggcc agtggccgcc tgcggatga gcagactgct gggggggacg 181 ctggagcgcg tctgcaaggc tgtgctcctt ctctgcctgc tgcacttcct
cgtggccgtc 241 atcctctact ttgacgtcta cgccagcac ctggccttc cgccacgctt cagtgccccga 301 ggccctgccc atgcctccca cccagctgct agcagcagca
gcagcagcag caactgctcc 361 cggccaacg ccacgcctc tagctccggg ctccagtgc cctgccagt 421 cccagcgctc caacgctgcc accctgtcct
gactgccac ctgtcttgt gggcagactg 481 ctgatcgagt tcacctcacc catgccccctg gagcggtgc agaggagaa cccaggcgtg 541 ctcatgggcg gccgatacac
accgcccgac tgcacccccag cccagacggt ggcggtcatc 601 atcccccttta gacaccgga acaccactg cgctactggc tccactatct acaccccatc 661 ttgaggcgc
agcggctgcg ctacggcgtc tatgtcatca accagcatgg tggagacatg 721 ttcaaccgg ccaagctgct taacgtggc ttcctagagg cgctgaagga ggatgccgcc 781
tatgactgct tcatcttcag cgatgtggac ctggctccca tggttcatg aggctcagtt 841 cgctgggcg accaaccccg ccactttgcc attgccatgg acaagtttgg cttccggctt 901
ccctatgctg gctacttgg agtgtgtca ggctgatgaa gatctcacgc ccagacatcc 961 aatgcttcc ccaatgagta ctgggctg ggtggcgagg atgatgacat cttcaaccgg
1021 atctccctga ctggatgaa gatctcacgc gaatcggccg ctacgcatg 1081 atcaagcacg accgacaa gcataacgaa cctaaccctc agaggttac
caagattcaa 1141 aacacgaagc tgaccatgaa gcgggacgc attgggtcag tgcggtacca ggtcttggag 1201 gtgtctcggc aaccactctt caccaatatc acagtggaca
ttgggcggcc tccgtcgtgg 1261 ccccctcggg gctgacacta atgacagag gctctcggtg ccgaagatg ctctcggtg 1321 gactgaccac agcctggctg gcagctgctc
tgtggaggac ctccagggact gagactgggc 1381 tctgtttttcc aagggtcttc actaggccc ctagccagcc ctggaagtt cagaaccac 1441 tttggggggc ctcctgcctg
ggcaggtct taagtgtgg ccctcttggg agtcaaccct 1501 ccttccccgac cccctccccc tagcccagcc ccagtcactg ctgaagggt gccagccct 1561 gcactgcctc
gcagagtgc ctgggctagg tcactccacc tctctgtgcc tcagtttccc 1621 cccttgagt ccctcccagc ctggaagggt ggaaggtatg tctagggggc agtgtctctt 1681
ccaggggaa ttccagctc ttgggaaacc cctgctcccc agggaggag aaacctttt 1741 cattcaacat tgtaggggac aagctttggt gcgccccctg ctgaaggagca gccccaggag
1801 gggaccagag gggatctgt gtctgctcct ggatctttgg ggtggccctt tgcatgggag 1861 gcagtggggg cttgatcag taagtctgt tcccgcctcc ctgtctgaga
gaggaggcag 1921 gagcccccagg gccggcttgt gtttgtacat tgcacagaaa ctttgtgtgg tgctttagta 1981 aaaaacgtga atgaaaaaa aaaaaaaaaa aaa

Figure 7

SEQ ID NO: 6

MSRLLGGTLERVCKAVLLLCLLHFLVAVILYFDVYAQHLAFFSR FSARGPAHALHPAASSSSSSNCSRPNATA
SSSGLPEVPSALPGPTAPTLPPCPDSPP GLVGRLLIEFTSPMPLERVQRENPGVLMGGRYTPPDCTPAQTVAVIIPFRHREHHLRY
WLHYLHPILRRQRLRYGVYVINQHGEDTFNRAKLLNVGFLEALKEDAAYDCFIFSDVD
LVPMDDRNLYRCGDQPRHFAIAMDKFGFRLPYAGYFGGVSGLSKAQFLRINGFPNEYW
GWGGEDDDIFNRISLTGMKISRPDIRIGRYRMIKHDRDKHNEPNPQRFTKIQNTKLTM KRDGIGSVRYQVLEVSRQP
LFTNITVDIGRPPSWPPRG

BETA 1,4-GALACTOSYLTRANSFERASES WITH ALTERED DONOR AND ACCEPTOR SPECIFICITIES, COMPOSITIONS AND METHODS OF USE

STATEMENT OF RIGHTS TO INVENTIONS MADE UNDER FEDERALLY SPONSORED RESEARCH

Research supporting this application was carried out by the United States of America as represented by the Secretary, Department of Health and Human Services. This research was supported by the Intramural Research Program of the NIH, National Cancer Institute, Center for Cancer Research. This research has been funded in part with Federal funds from the National Cancer Institute, NIH, under contract No. N01-C0-12400.

RELATED APPLICATIONS

This application is a 35 U.S.C. §371 U.S. national entry of International Application PCT/US2007/018656 (WO 2009/025645) having an International filing date of Aug. 22, 2007 which application is incorporated herein in its entirety by reference.

FIELD OF THE INVENTION

The invention relates generally to beta (1,4)-galactosyltransferase I enzymes having altered donor and acceptor specificities, and methods of use thereof. In addition, the invention relates to methods for synthesizing oligosaccharides using the beta (1,4)-galactosyltransferase I enzymes and to using these beta (1,4)-galactosyltransferase I mutants to conjugate agents, such as therapeutic agents or diagnostic agents, to acceptor molecules.

BACKGROUND OF THE INVENTION

The present invention relates to the field of glycobiology, specifically to glycosyltransferases, a superfamily of enzymes involved in synthesizing carbohydrate moieties of glycoproteins, glycolipids and glycosaminoglycans. The present invention provides structure-based design of novel glycosyltransferases and their biological applications.

Glycans can be classified as linear or branched sugars. The linear sugars are the glycosaminoglycans comprising polymers of sulfated disaccharide repeat units that are O-linked to a core protein, forming a proteoglycan aggregate (Raman et al. 2005). The branched glycans are found as N-linked and O-linked sugars on glycoproteins or on glycolipids (Lowe et al., 2003). These carbohydrate moieties of the linear and branched glycans are synthesized by a super family of enzymes, the glycosyltransferases, which transfer a sugar moiety from a sugar donor to an acceptor molecule.

Eukaryotic cells express several classes of oligosaccharides attached to proteins or lipids. Animal glycans can be N-linked via beta-GlcNAc to Asn (N-glycans), O-linked via -GalNAc to Ser/Thr (O-glycans), or can connect the carboxyl end of a protein to a phosphatidylinositol unit (GPI-anchors) via a common core glycan structure. Beta (1,4)-galactosyltransferase I catalyzes the transfer of galactose from the donor, UDP-galactose, to an acceptor, N-acetylglucosamine, to form a galactose-beta (1,4)-N-acetylglucosamine bond, and thus allows galactose to be linked to an N-acetylglucosamine that may itself be linked to a variety of other molecules. Examples of such molecules include other sugars and proteins. This reaction can be used to make many types of molecules with biological significance. For example, galactose-beta (1,4)-N-acetylglucosamine linkages are important for many recognition events that control how cells interact with each other in the body, and how cells interact with pathogens. In addition, numerous other linkages of this type play a role in cellular recognition and binding events, as well as in cellular interactions with pathogens, such as viruses.

The structural information of glycosyltransferases has revealed that the specificity of the sugar donor in these enzymes is determined by a few residues in the sugar-nucleotide binding pocket of the enzyme, which is conserved among the family members from different species. This conservation has made it possible to reengineer the existing glycosyltransferases with broader sugar donor specificities. Mutation of these residues generates novel glycosyltransferases that can transfer a sugar residue with a chemically reactive functional group to N-acetylglucosamine (GlcNAc), galactose (Gal) and xylose residues of glycoproteins, glycolipids and proteoglycans (glycoconjugates). Thus, there is potential to develop mutant glycosyltransferases to produce glycoconjugates carrying sugar moieties with reactive groups that can be used in the assembly of bio-nanoparticles to develop targeted-drug delivery systems or contrast agents for medical uses.

Accordingly, methods to synthesize N-acetylglucosamine linkages have many applications in research and medicine, including in the development of pharmaceutical agents and improved vaccines that can be used to treat disease.

SUMMARY OF THE INVENTION

As described below, the present invention describes a double mutant beta 1,4 galactosyltransferase, human beta-1,4-Tyr285Leu-Met340His-Gal-T1, constructed from the individual mutants, Tyr285Leu-Gal-T1 and Met340His-Gal-T1, that transfers modified galactose in the presence of magnesium ion. The invention is based on the structure-based design of beta 1,4-Galactosyltransferase I (beta4Gal-TI) that is dependent on magnesium for its activity, and is equally efficient as N-Acetylgalactosaminyltransferase in activity. The invention is based further on the novel finding that the point mutations Tyr 285 to Leu 285 and Met 340 to His340 of human beta Gal-TI (Gal-TI-Y285L-M340H), changes the metal requirement from manganese to magnesium and broadens the sugar donor specificity towards N-acetylgalactosamine and 2'-modified galactose. In particular, the invention describes a double mutant that can transfer galactose and GalNAc as efficiently from its UDP-derivatives in the presence of magnesium.

Accordingly, in a first aspect the invention provides a polypeptide fragment of a beta (1,4)-galactosyltransferase I that retains the ability to transfer GalNAc or galactose from a sugar donor to a sugar acceptor in the presence of magnesium.

In one embodiment, the polypeptide fragment comprises an amino acid substitution at amino acid positions 285 and 340 corresponding to human beta (1,4)-galactosyltransferase I (SEQ ID NO: 2). In another embodiment, the polypeptide fragment comprises a conservative amino acid substitution at amino acid positions 289 and 344 corresponding to bovine beta (1,4)-galactosyltransferase I (SEQ ID NO: 2).

In a related embodiment, a leucine (L) is substituted for a tyrosine (Y) at amino acid position 285 and a methionine (M) is substituted for a histidine (H) at amino acid position 340 (SEQ ID NO: 3). In another related embodiment, a leucine (L) is substituted for a tyrosine (Y) at amino acid position 289 and a methionine (M) is exchanged for a histidine (H) at amino acid position 344 (SEQ ID NO: 4).

In another aspect, the invention provides a polypeptide fragment of a beta (1,4)-galactosyltransferase I that retains the ability to transfer GalNAc or galactose from a sugar donor to a sugar acceptor, wherein the polypeptide fragment comprises SEQ ID NO: 2.

In one embodiment of the above aspects, the sugar donor is selected from UDP-GalNAc, UDP-galactose, UDP-GalNAc analogues or UDP-galactose analogues. In another embodiment, the UDP-galactose analogue or the UDP-GalNAc analogue comprises an azido group, a keto group, or a thiol group. In a related embodiment, the azido group, the keto group or the thiol group is substituted at the C2 position of galactose. In another related embodiment, one or more agents are linked to a sugar moiety of the sugar donor.

In another embodiment, the agent is selected from the group consisting of: antibodies, single chain antibodies, bacterial toxins, growth factors, therapeutic agents, targeting agents, contrast agents, chemical labels, a radiolabels, and fluorescent labels.

In a related embodiment, the transfer occurs in the presence of magnesium.

In still another related embodiment, the sugar acceptor is N-acetylglucosamine (GlcNAc). In a further embodiment, the N-acetylglucosamine (GlcNAc) is free or attached to a peptide of a glycopeptide.

In another aspect, the invention provides a polypeptide fragment from a beta 1,4-galactosyltransferase I that catalyzes the formation of a GalNAc-beta-1,4-N-acetylgalactosamine bond in the presence of magnesium.

In one embodiment, the polypeptide fragment comprises SEQ ID NO: 2.

In another aspect, the invention provides a nucleic acid molecule comprising SEQ ID NO: 1.

In still another aspect, the invention provides an isolated amino acid sequence corresponding to the polypeptide fragment of claim 15 comprising SEQ ID NO: 2.

In one embodiment, an expression cassette or vector comprises a nucleic acid molecule described herein.

In another aspect, the invention features an expression cassette or vector comprising a nucleic acid segment encoding a polypeptide fragment of a beta (1,4)-galactosyltransferase I that transfers GalNAc or galactose from a sugar donor to a sugar acceptor, wherein the sugar donor comprises UDP-GalNAc, UDP-Galactose, UDP-GalNAc analogue or a UDP-Galactose analogue, in the presence of magnesium or that catalyzes the formation of a GalNAc- or Gal-beta-1,4-N-acetylgalactosamine bond in the presence of magnesium.

In one embodiment, a host cell comprises a expression cassette or vector as described herein.

In another aspect, the invention features a method of making a glycoprotein comprising incubating a reaction mixture comprising a polypeptide fragment from a beta (1,4)-galactosyltransferase I with a sugar donor and a sugar acceptor in the presence of magnesium.

In one embodiment, the polypeptide fragment comprises an amino acid exchange at amino acid positions 285 and 340 corresponding to human beta (1,4)-galactosyltransferase I (SEQ ID NO: 3).

In another embodiment, the polypeptide fragment comprises a conservative amino acid exchange at amino acid positions 289 and 344 corresponding to bovine beta (1,4)-galactosyltransferase I (SEQ ID NO: 4).

In another embodiment, a leucine (L) is exchanged for a tyrosine (Y) at amino acid position 285 and a methionine (M) is exchanged for a histidine (H) at amino acid position 340 of (SEQ ID NO: 3).

In a further embodiment, a leucine (L) is exchanged for a tyrosine (Y) at amino acid position 289 and a methionine (M) is exchanged for a histidine (H) at amino acid position 344 of (SEQ ID NO: 4).

In another aspect, the invention features a method of making a glycoprotein comprising incubating a reaction mixture comprising a polypeptide fragment from a beta (1,4)-galactosyltransferase I, wherein the polypeptide fragment comprises SEQ ID NO: 2, with a sugar donor and an sugar acceptor.

In one embodiment, the sugar donor is selected from UDP-GalNAc, UDP-galactose, UDP-GalNAc analogues or UDP-galactose analogues.

In another embodiment, the UDP-galactose analogue or UDP-GalNAc analogue comprises an azido group, a keto group, or a thiol group.

In another embodiment, the azido group, the keto group or the thiol group is substituted at the C2 position of galactose.

In yet another embodiment, the one or more agents are linked to a sugar moiety of the sugar donor.

In one embodiment, the agent is selected from the group consisting of: antibodies, single chain antibodies, bacterial toxins, growth factors, therapeutic agents, contrast agents, targeting agents, chemical labels, a radiolabels, and fluorescent labels.

In a particular embodiment, the transfer occurs in the presence of magnesium.

In another particular embodiment, the sugar acceptor is N-acetylglucosamine (GlcNAc). In a further embodiment, the N-acetylglucosamine (GlcNAc) is free or attached to a peptide of a glycopeptide.

In another aspect, the invention features a method of making a glycoprotein comprising incubating a reaction mixture comprising a polypeptide fragment of a beta 1,4-galactosyltransferase I that catalyzes the formation of a GalNAc beta-1,4-N-acetylgalactosamine bond with a sugar donor, in the presence of magnesium.

In one embodiment, the polypeptide fragment comprises SEQ ID NO: 2.

In another aspect, the invention features a method to of making a glycoprotein comprising incubating a reaction mixture comprising a polypeptide fragment from a beta (1,4)-galactosyltransferase I, wherein the polypeptide fragment comprises SEQ ID NO: 2, with a sugar donor, wherein the sugar donor comprises a UDP-galactose, UDP-GalNAc, UDP-GalNAc analogue or a UDP-Gal analogue, and a N-acetylglucosamine sugar acceptor in the presence of magnesium.

In still another aspect, the invention features an isolated glycoprotein synthesized by the method comprising incubating a reaction mixture comprising a polypeptide fragment from a beta (1,4)-galactosyltransferase I with a sugar donor and a sugar acceptor in the presence of magnesium.

In one embodiment, the polypeptide fragment comprises an amino acid exchange at amino acid positions 285 and 340 corresponding to human beta (1,4)-galactosyltransferase I (SEQ ID NO: 3).

In another embodiment, the polypeptide fragment comprises a conservative amino acid exchange at amino acid positions 289 and 344 corresponding to bovine beta (1,4)-galactosyltransferase I (SEQ ID NO: 4).

In another embodiment, a leucine (L) is exchanged for a tyrosine (Y) at amino acid position 285 and a methionine (M) is exchanged for a histidine (H) at amino acid position 340 of (SEQ ID NO: 3).

In a further embodiment, a leucine (L) is substituted for a tyrosine (Y) at amino acid position 289 and a methionine (M) is exchanged for a histidine (H) at amino acid position 344 of (SEQ ID NO: 4).

In another aspect, the invention features a glycoprotein synthesized by a method comprising incubating a reaction mixture comprising a polypeptide fragment of a beta (1,4)-galactosyltransferase I, wherein the polypeptide fragment comprises SEQ ID NO: 2, with a sugar donor and an sugar acceptor.

In one embodiment, the sugar donor is selected from UDP-GalNAc, UDP-galactose, UDP-GalNAc analogues or UDP-galactose analogues. In a further embodiment, the UDP-GalNAc or UDP-galactose analogue comprises an azido group, a keto group, or a thiol group. In a related embodiment, the azido group, the keto group or the thiol group is substituted at the C2 position of galactose.

In another embodiment, one or more agents are linked to a sugar moiety of the sugar donor. In a related embodiment, the agent is selected from the group consisting of: antibodies, single chain antibodies, bacterial toxins, growth factors, therapeutic agents, contrast agents, targeting agents, chemical labels, a radiolabels, and fluorescent labels.

In one embodiment, the transfer occurs in the presence of magnesium.

In another embodiment, the sugar acceptor is N-acetylglucosamine (GlcNAc). In a further embodiment, the N-acetylglucosamine (GlcNAc) is free or attached to a peptide of a glycopeptide.

In another aspect, the invention features a glycoprotein synthesized by the method comprising incubating a reaction mixture comprising a polypeptide fragment from a beta 1,4-galactosyltransferase I that catalyzes the formation of a GalNAc- or beta-1,4-N-acetylgalactosamine bond in the presence of magnesium.

In one embodiment, the polypeptide fragment comprises SEQ ID NO: 2.

In another aspect, the invention features a glycoprotein synthesized by the method comprising incubating a reaction mixture comprising a polypeptide fragment from a beta (1,4)-galactosyltransferase I, wherein the polypeptide fragment comprises SEQ ID NO: 1, with a sugar donor, wherein the sugar donor comprises UDP-GalNAc, or a UDP-GalNAc analogue, and a N-acetylglucosamine sugar acceptor in the presence of magnesium.

In another aspect, the invention features a composition comprising a polypeptide fragment of a beta (1,4)-galactosyltransferase I that transfers GalNAc or galactose from a sugar donor to a sugar acceptor in the presence of magnesium.

In one embodiment, the polypeptide fragment comprises an amino acid substitution at amino acid positions 285 and 340 corresponding to human beta (1,4)-galactosyltransferase I (SEQ ID NO: 3).

In another embodiment, the polypeptide fragment comprises a conservative amino acid substitution at amino acid positions 289 and 344 corresponding to bovine beta (1,4)-galactosyltransferase I (SEQ ID NO: 4).

In another embodiment, a leucine (L) is substituted for a tyrosine (Y) at amino acid position 285 and a methionine (M) is substituted for a histidine (H) at amino acid position 340 of (SEQ ID NO: 3).

In another embodiment, a leucine (L) is substituted for a tyrosine (Y) at amino acid position 289 and a methionine (M) is substituted for a histidine (H) at amino acid position 344 of (SEQ ID NO: 4).

In another aspect, the invention features a composition comprising a polypeptide fragment from a beta (1,4)-galactosyltransferase I that transfers GalNAc or galactose from a sugar donor to a sugar acceptor, wherein the polypeptide fragment comprises SEQ ID NO: 2.

In one embodiment, the sugar donor is selected from UDP-GalNAc, UDP-galactose, UDP-GalNAc analogue or UDP-galactose analogue.

In another embodiment, the UDP-GalNAc analogue or the UDP-galactose analogue comprises an azido group, a keto group, or a thiol group. In another embodiment, the azido group, the keto group or the thiol group is substituted at the C2 position of galactose.

In another embodiment, one or more agents are linked to a sugar moiety of the sugar donor. In another related embodiment, the agent is selected from the group consisting of: antibodies, single chain antibodies, bacterial toxins, growth factors, therapeutic agents, targeting agents, contrast agents, chemical labels, a radiolabels, and fluorescent labels.

In one embodiment, the transfer occurs in the presence of magnesium.

In another embodiment, the sugar acceptor is N-acetylglucosamine (GlcNAc).

In another embodiment, the N-acetylglucosamine (GlcNAc) is free or attached to a peptide of a glycopeptide.

In another aspect, the invention features a composition comprising a polypeptide fragment of a beta 1,4-galactosyltransferase I that catalyzes the formation of a GalNAc-beta-1,4-N-acetylgalactosamine bond in the presence of magnesium.

In one embodiment, the polypeptide fragment comprises SEQ ID NO: 2.

In another embodiment, the composition further comprises an adjuvant.

In another aspect, the invention features a method of coupling an agent to a carrier protein comprising incubating a reaction mixture comprising a polypeptide fragment of a beta (1,4)-galactosyltransferase I, wherein the polypeptide fragment comprises SEQ ID NO: 2, with a sugar donor, and a carrier protein, in the presence of magnesium.

In one embodiment, the sugar donor is a UDP-GalNAc analogue or a UDP-galactose analogue.

In another embodiment, the UDP-GalNAc analogue or the UDP-galactose analogue comprises an azido group, a keto group, or a thiol group. In a related embodiment, the azido group, the keto group or the thiol group is substituted at the C2 position of galactose.

In another embodiment, one or more agents are linked to a sugar moiety of the sugar donor. In a related embodiment, the agent is selected from the group consisting of: antibodies, single chain antibodies, bacterial toxins, growth factors, therapeutic agents, targeting agents, contrast agents, chemical labels, a radiolabels, and fluorescent labels.

In one embodiment, the carrier protein is ovalbumin. In another embodiment, the carrier protein is an IgG.

In another embodiment, the method comprises the steps of coupling the C2 UDP-galactose analogue to biotin for detection.

In another further embodiment, the detection is by chemiluminescent assay. In a related embodiment, the contrast agent is a paramagnetic contrast agent. In another related embodiment, the paramagnetic contrast agent is used in magnetic resonance imaging.

In another aspect, the invention features a method for the diagnosis or treatment of a subject having a disease or disorder comprising administering to the subject an effective amount of polypeptide fragment synthesized by the method comprising incubating a reaction mixture comprising an polypeptide fragment from a beta (1,4)-galactosyltransferase I with a sugar donor, wherein one or more agents are linked to the sugar donor, and an sugar acceptor thereby diagnosing or treating the subject.

In one embodiment, the polypeptide fragment comprises an amino acid exchange at amino acid positions 285 and 340 corresponding to human beta (1,4)-galactosyltransferase I (SEQ ID NO: 3).

In another embodiment, the polypeptide fragment comprises a conservative amino acid exchange at amino acid positions 289 and 344 corresponding to bovine beta (1,4)-galactosyltransferase I (SEQ ID NO: 4).

In another embodiment, a leucine (L) is exchanged for a tyrosine (Y) at amino acid position 285 and a methionine (M) is exchanged for a histidine (H) at amino acid position 340 of (SEQ ID NO: 3).

In another embodiment, a leucine (L) is exchanged for a tyrosine (Y) at amino acid position 289 and a methionine (M) is exchanged for a histidine (H) at amino acid position 344 of (SEQ ID NO: 4).

In another aspect, the invention features a method for the diagnosis or treatment of a subject suffering from a disease or disorder comprising administering to the subject an effective amount of a polypeptide fragment synthesized by a method comprising incubating a reaction mixture comprising a polypeptide fragment of a beta (1,4)-galactosyltransferase I, wherein the polypeptide fragment comprises SEQ ID NO: 2, with a sugar donor, wherein the sugar donor comprises UDP-Galactose analogue and wherein one or more agents are linked to the sugar donor, and an sugar acceptor in the presence of magnesium, thereby diagnosing or treating the subject.

In one embodiment, the sugar donor is a UDP-GalNAc analogue or a UDP-galactose analogue. In another embodiment, the UDP-GalNAc analogue or the UDP-galactose analogue comprises an azido group, a keto group, or a thiol group. In a related embodiment, the azido group, the keto group or the thiol group is substituted at the C2 position of galactose.

In another embodiment, one or more agents are linked to a sugar moiety of the sugar donor. In a related embodiment, the agent is selected from the group consisting of: antibodies, single chain antibodies, bacterial toxins, growth factors, therapeutic agents, targeting agents, contrast agents, chemical labels, a radiolabels, and fluorescent labels.

In a further embodiment, the transfer occurs in the presence of magnesium.

In another embodiment, the sugar acceptor is N-acetylglucosamine (GlcNAc). In a related embodiment, the N-acetylglucosamine (GlcNAc) is free or attached to a peptide of a glycopeptide.

In another aspect, the invention features a method for the diagnosis or treatment of a subject suffering from a disease or disorder comprising administering to the subject an effective amount of a polypeptide fragment synthesized by a method comprising incubating a reaction mixture comprising a polypeptide fragment of a beta 1,4-galactosyltransferase I that catalyzes the formation of a GlcNAc-beta-1,4-N-acetylgalactosamine bond in the presence of magnesium and a sugar donor, wherein the sugar donor comprises a UDP-GalNAc or a UDP-GalNAc analogue, and wherein one or more agents are linked to the sugar donor.

In one embodiment, the polypeptide fragment comprises SEQ ID NO: 2.

In another embodiment, at least two agents are linked to the sugar donor. In a further embodiment, the agents comprise at least a targeting agent and a therapeutic agent.

In another aspect, the invention features a method for imaging a target cell or tissue in a subject comprising administering to a subject a polypeptide fragment synthesized by a method comprising incubating a reaction mixture comprising a polypeptide fragment of a beta (1,4)-galactosyltransferase I with a sugar donor, wherein one or more imaging agents are linked to the sugar donor, and an sugar acceptor and thereby imaging a target cell or tissue.

In one embodiment, the polypeptide fragment comprises an amino acid exchange at amino acid positions 285 and 340 corresponding to human beta (1,4)-galactosyltransferase I (SEQ ID NO: 3).

In another embodiment, the polypeptide fragment comprises a conservative amino acid exchange at amino acid positions 289 and 344 corresponding to bovine beta (1,4)-galactosyltransferase I (SEQ ID NO: 4).

In another embodiment, a leucine (L) is exchanged for a tyrosine (Y) at amino acid position 285 and a methionine (M) is exchanged for a histidine (H) at amino acid position 340 of (SEQ ID NO: 3).

In another embodiment, a leucine (L) is exchanged for a tyrosine (Y) at amino acid position 289 and a methionine (M) is exchanged for a histidine (H) at amino acid position 344 of (SEQ ID NO: 4).

In another aspect, the invention features a method for imaging a target cell or tissue comprising administering to a subject a polypeptide fragment synthesized by a method comprising incubating a reaction mixture comprising a polypeptide fragment of a beta (1,4)-galactosyltransferase I, wherein the polypeptide fragment comprises SEQ ID NO: 2, with a sugar donor, and wherein one or more imaging agents are linked to the sugar donor, and an sugar acceptor in the presence of magnesium, thereby imaging a target cell or tissue.

In one embodiment, the sugar donor is a UDP-GalNAc analogue or a UDP-galactose analogue.

In another embodiment, the UDP-GalNAc analogue UDP-galactose analogue comprises an azido group, a keto group, or a thiol group.

In another embodiment, the azido group, the keto group or the thiol group is substituted at the C2 position of galactose. In a related embodiment, one or more imaging agents are linked to a sugar moiety of the sugar donor. In another embodiment, the imaging agent is selected from the group consisting of: chemical labels, radiolabels, and fluorescent labels.

In another embodiment, the transfer occurs in the presence of magnesium.

In another embodiment, the sugar acceptor is N-acetylglucosamine (GlcNAc). In a related embodiment, the N-acetylglucosamine (GlcNAc) is free or attached to a peptide of a glycopeptide.

In another aspect, the invention features a method for imaging a target cell or tissue comprising administering to a subject a polypeptide fragment synthesized by a method comprising incubating a reaction mixture comprising a polypeptide fragment of a beta 1,4-galactosyltransferase I that catalyzes the formation of a GlcNAc-beta-1,4-N-acetylgalactosamine bond in the presence of magnesium and a sugar donor, wherein the sugar donor comprises a UDP-galactose analogue, and wherein one or more imaging agents are linked to the sugar donor.

In one embodiment, the polypeptide fragment comprises SEQ ID NO: 2.

In another aspect, the invention features a method for preventing platelet aggregation comprising administering to a subject an effective amount of a polypeptide fragment synthesized by the method comprising incubating a reaction mixture comprising a polypeptide fragment from a beta (1,4)-galactosyltransferase I with a sugar donor and an sugar acceptor and thereby preventing platelet aggregation.

In one embodiment, the polypeptide fragment comprises an amino acid exchange at amino acid positions 285 and 340 corresponding to human beta (1,4)-galactosyltransferase I (SEQ ID NO: 3).

In another embodiment, the polypeptide fragment comprises a conservative amino acid exchange at amino acid positions 289 and 344 corresponding to bovine beta (1,4)-galactosyltransferase I (SEQ ID NO: 4).

In another embodiment, a leucine (L) is exchanged for a tyrosine (Y) at amino acid position 285 and a methionine (M) is exchanged for a histidine (H) at amino acid position 340 of (SEQ ID NO: 3).

In another embodiment, a leucine (L) is exchanged for a tyrosine (Y) at amino acid position 289 and a methionine (M) is exchanged for a histidine (H) at amino acid position 344 of (SEQ ID NO: 4).

In another aspect, the invention features a method for preventing platelet aggregation comprising administering to a subject an effective amount of a polypeptide fragment synthesized by the method comprising incubating a reaction mixture comprising a polypeptide fragment of a beta (1,4)-galactosyltransferase I, wherein the polypeptide fragment comprises SEQ ID NO: 2, with a sugar donor, wherein the sugar donor comprises a UDP-GalNAc analogue or a UDP-galactose analogue and a sugar acceptor in the presence of magnesium, and thereby preventing platelet aggregation.

In one embodiment, the sugar donor is a UDP-GalNAc analogue or a UDP-galactose analogue.

In another embodiment, the sugar acceptor is N-acetylglucosamine (GlcNAc).

In another embodiment, the N-acetylglucosamine (GlcNAc) is free or attached to a peptide of a glycopeptide.

In another aspect, the invention features a method for preventing platelet aggregation comprising administering to the subject an effective amount of an isolated glycoprotein synthesized by the method comprising incubating a reaction mixture comprising an polypeptide fragment from a beta 1,4-galactosyltransferase I that catalyzes the formation of a GlcNAc-beta-1,4-N-acetylgalactosamine bond and a sugar donor, wherein the sugar donor comprises UDP-GalNAc or a UDP-GalNAc analogue.

In one embodiment, the polypeptide fragment comprises SEQ ID NO: 2.

In another embodiment, the subject is suffering from abnormal platelet aggregation caused by a genetic lesion.

In another embodiment, the subject is suffering from abnormal platelet aggregation caused by a drug treatment.

In another aspect, the invention features a method for inducing an immune response in a subject comprising administering to the subject a composition as described in the aspects herein.

In another aspect, the invention features a kit comprising packaging material, and a polypeptide fragment from a beta (1,4)-galactosyltransferase I according to any one of the above-mentioned aspects.

In one embodiment, the kit further comprises a sugar donor.

In another embodiment, the donor is selected from the group consisting of UDP-galactose, UDP-GalNAc, UDP-GalNAc analogues or UDP-Galactose analogues.

In another embodiment, an agent is linked to the sugar donor.

In a further embodiment, the agent is selected from the group consisting of antibodies, single chain antibodies, bacterial toxins, growth factors, therapeutic agents, contrast agents, targeting agents, chemical labels, a radiolabels, and fluorescent labels.

BRIEF DESCRIPTION OF THE DRAWINGS

FIG. 3 shows the catalytic domain corresponding to amino acids 127-398 of the double substitution human beta-4Gal-T1-M340H-Y285L. FIG. 3A shows the DNA sequence corresponding to the protein sequence, amino acid residues 127 to 398 (SEQ ID NO: 1). FIG. 3B shows the protein sequence corresponding to amino acid residues 127 to 398 (SEQ ID NO: 2).

FIG. 4 shows the amino acid sequence corresponding to human beta 1,4 galactosyltransferase-I (SEQ ID NO: 3).

FIG. 5 shows the amino acid sequence corresponding to bovine beta 1,4 galactosyltransferase-I (SEQ ID NO: 4).

FIG. 6 shows the nucleotide sequence corresponding to human beta 1,4 galactosyltransferase-I (SEQ ID NO: 5).

FIG. 7 shows the amino acid sequence corresponding to human beta 1,4 galactosyltransferase-I (SEQ ID NO: 6).

DETAILED DESCRIPTION OF THE INVENTION

Figure 1:
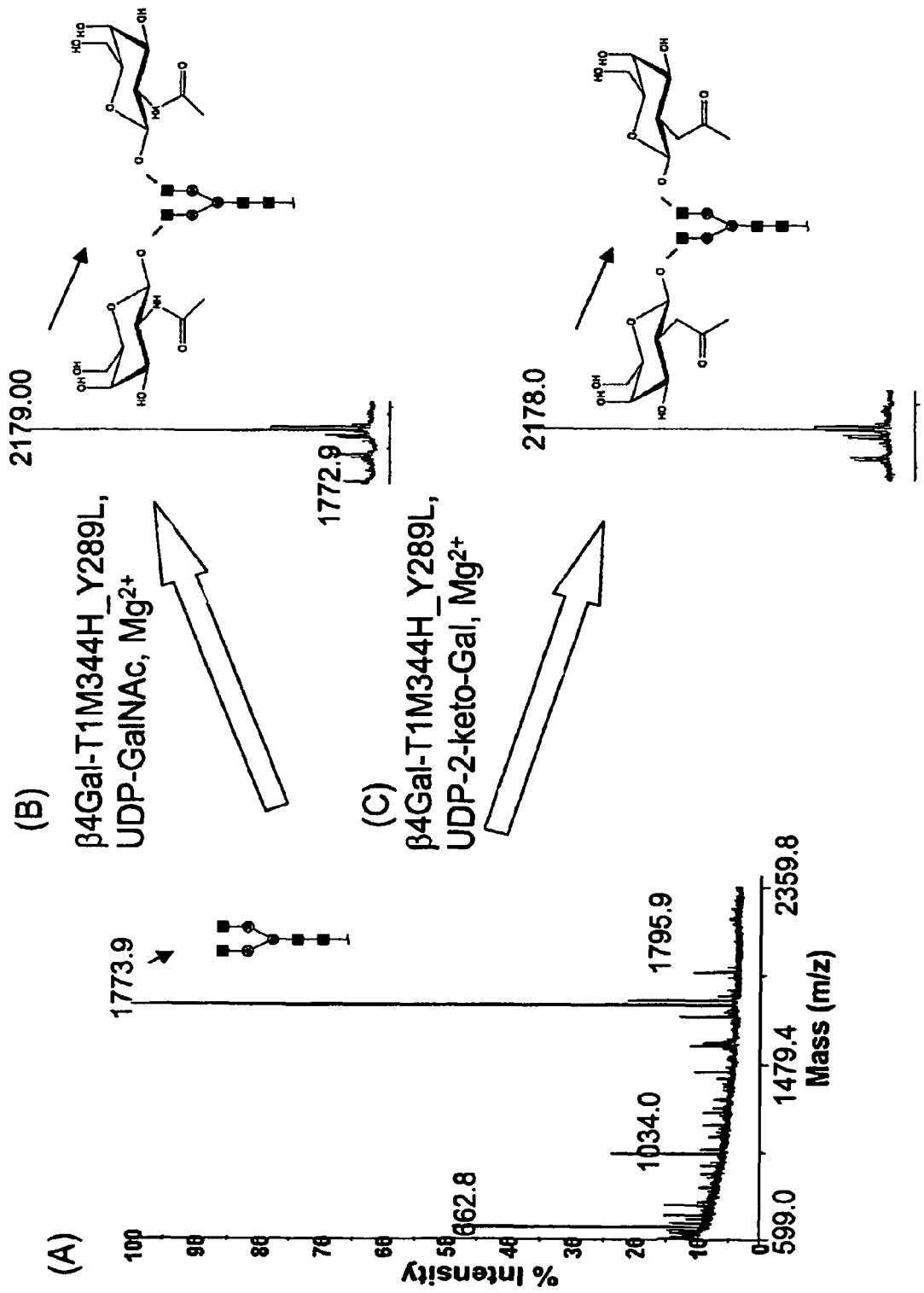
FIG. 1 (A-C) shows the MALDI mass spectra of glycans after the transfer of GalNAc (B) or 2-keto-galactose (C) to the sugar acceptor, heptasaccharide tetrapeptide (A), Arg-[GlcNAcβ1,2-Manα1,6-(GlcNAcβ1,2-Manα1,3)-Manβ1,4-GlcNAcβ1,4-GlcNAcβ]-Asn-Glu-Gly, by the double substitution enzyme, human beta 4Gal-T1M340H_Y285L. *Major* peaks are annotated with the carbohydrate structure shown in the symbols for monosaccharides, according to the nomenclature adopted by the consortium for functional glycomics, (on the world wide web at functionalglycomics.org/static/consortium/). GlcNAc (squares), mannose (spheres).

The invention generally features beta (1,4)-galactosyltransferase I enzymes having altered donor and acceptor specificities, and methods of use thereof. In addition, the invention relates to methods for synthesizing oligosaccharides using the beta (1,4)-galactosyltransferase I enzymes as described herein and to using the beta (1,4)-galactosyltransferase I enzymes to conjugate agents, such as therapeutic agents or diagnostic agents, to acceptor molecules. The glycoconjugates have use in, for example, disease treatment, diagnostics, and imaging.

Definitions

The invention is better understood with the aid of the following definitions.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used in the specification and claims, the singular form "a", "an" and "the" include plural references unless the context clearly dictates otherwise. For example, the term "a cell" includes a plurality of cells, including mixtures thereof. The term "a nucleic acid molecule" includes a plurality of nucleic acid molecules.

As used herein, the term "comprising" is intended to mean that the compositions and methods include the recited elements, but do not exclude other elements. "Consisting essentially of", when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

The term "acceptor" is meant to refer to a molecule or structure onto which a donor is actively linked through action of a of a galactosyltransferase, or fragment thereof. Examples of acceptors include, but are not limited to, carbohydrates, glycoproteins, glycolipids. In preferred embodiments, the acceptor polypeptide can comprise, N-acetylglucosamine (GlcNAc) residues, free or attached to a peptide or glycopeptide.

The term "agent" or "bioactive agent" is meant to refer to any chemical or biological material or compound that is suitable for delivery that induces a desired effect in or on an organism, such as a biological or pharmacological effect, which may include, but is not limited to a prophylactic effect, alleviating a condition caused by a disease or a disorder, reducing or eliminating a disease or disorder. An agent or a bioactive agent refers to substances that are capable of exerting a biological effect in vitro and/or in vivo. Examples include diagnostic agents, pharmaceuticals, drugs, synthetic organic molecules, proteins, peptides, vitamins, steroids, genetic material including nucleotides, nucleosides, polynucleotides, RNAs, siRNAs, shRNAs, anti-sense DNA or RNA.

The term "antibody" as used herein refers to both polyclonal and monoclonal antibody. The term can also refer to single chain antibodies. The term encompasses not only intact immunoglobulin molecules, but fragments and genetically engineered derivatives of immunoglobulin molecules as may be prepared by techniques known in the art, and which retains the binding specificity of the antigen binding site.

The term "fragment" refers to an amino acid segment of a beta (1,4)-galactosyltransferase I enzyme which is able to catalyze the linkage of a donor to an acceptor. A fragment may be from any mammalian beta (1,4)-galactosyltransferase I. In certain embodiments, the catalytic domain is from bovine beta (1,4)-galactosyltransferase I, in other certain embodiments, the catalytic domain is from human beta (1,4)-galactosyltransferase I. In preferred embodiments, a beta (1,4)-galactosyltransferase I fragment is encoded by SEQ ID NO: 1 or has the amino acid sequence of SEQ ID NO: 2.

The term "donor" refers to a molecule that is actively linked to an acceptor molecule through the action of a catalytic domain of a galactosyltransferase, or mutant thereof. A donor molecule can include a sugar, or a sugar derivative. Examples of donors include, but are not limited to, UDP-GalNAc, UDP-GalNAc analogues, UDP-galactose or UDP-galactose analogues. Donors include sugar derivatives that include agents, biological agents, or active groups. Accordingly, oligosaccharides may be prepared according to the methods of the invention that include a sugar derivative having any desired characteristic.

The term "effective amount" is meant to refer to a sufficient amount capable to provide the desired local or systemic effect.

The term "expression cassette" as used herein refers to a DNA sequence capable of directing expression of a particular nucleotide sequence in an appropriate host cell, comprising a promoter operably linked to the nucleotide sequence of interest that is operably linked to termination signals. It also typically comprises sequences required for proper translation of the nucleotide sequence. The expression cassette may be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

The term "beta-1,4 galactosyltransferase (beta 4Gal-T1)" as used herein refers to enzymes substantially homologous to, and having substantially the same biological activity as, the enzyme encoded by the nucleotide sequence depicted in SEQ ID NO: 1 and the amino acid sequence depicted in SEQ ID NO: 2. This definition is intended to encompass natural allelic variations in the beta 4Gal-T1 sequence, and all references to beta 4Gal-T1, and nucleotide and amino acid sequences thereof are intended to encompass such allelic variations, both naturally-occurring and man-made. The production of proteins such as the enzyme beta 4Gal-T1 from cloned genes by genetic engineering is well known.

The beta 4Gal-T1 enzyme may be synthesized in host cells transformed with vectors containing DNA encoding the beta 4Gal-T1 enzyme. A vector is a replicable DNA construct. Vectors are used herein either to amplify DNA encoding the beta 4Gal-T1 enzyme and/or to express DNA which encodes the beta 4Gal-T1 enzyme. An expression vector is a replicable DNA construct in which a DNA sequence encoding the beta 4Gal-T1 enzyme is operably linked to suitable control sequences capable of effecting the expression of the beta 4Gal-T1 enzyme in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

The term "immunogenic" compound or composition as used herein refers to a compound or composition that is capable of stimulating production of a specific immunological response when administered to a suitable host, usually a mammal.

The term "nucleic acid" is intended to include nucleic acid molecules, e.g., polynucleotides which include an open reading frame encoding a polypeptide, and can further include non-coding regulatory sequences, and introns. In addition, the terms are intended to include one or more genes that map to a functional locus. In addition, the terms are intended to include a specific gene for a selected purpose. The gene can be endogenous to the host cell or can be recombinantly introduced into the host cell, e.g., as a plasmid maintained episomally or a plasmid (or fragment thereof) that is stably integrated into the genome. In one embodiment, the gene of polynucleotide segment is involved sugar transfer. A mutant nucleic acid molecule is intended to include a nucleic acid molecule or gene having a nucleotide sequence which includes at least one alteration (e.g., substitution, insertion, deletion) such that the polypeptide or polypeptide that can be encoded by said mutant exhibits an activity that differs from the polypeptide or polypeptide encoded by the wild-type nucleic acid molecule or gene.

The terms "oligosaccharide" and "polysaccharide" are used interchangeably herein. These terms refer to saccharide chains having two or more linked sugars. Oligosaccharides and polysaccharides may be homopolymers and heteropolymers having a random sugar sequence or a preselected sugar sequence. Additionally, oligosaccharides and polysaccharides may contain sugars that are normally found in nature, derivatives of sugars, and mixed polymers thereof. "saccharide" refers to any of a series of compounds of carbon, hydrogen, and oxygen in which the atoms of the latter two elements are in the ratio of 2:1, especially those containing the group $C_6H_{10}O_5$, including fructose, glucose, sucrose, lactose, maltose, galactose and arabinose.

The terms "polypeptides" and "proteins" are used interchangeably herein. Polypeptides and proteins can be expressed in vivo through use of prokaryotic or eukaryotic expression systems. Many such expressions systems are known in the art and are commercially available. (Clontech, Palo Alto, Calif.; Stratagene, La Jolla, Calif.). Examples of such systems include, but are not limited to, the T7-expression system in prokaryotes and the bacculovirus expression system in eukaryotes. Polypeptides can also be synthesized in vitro, e.g., by the solid phase peptide synthetic method or by in vitro transcription/translation systems. Such methods are described, for example, in U.S. Pat. Nos. 5,595,887; 5,116,750; 5,168,049 and 5,053,133; Olson et al., Peptides, 9, 301, 307 (1988). The solid phase peptide synthetic method is an established and widely used method, which is described in the following references: Stewart et al., Solid Phase Peptide Synthesis, W. H. Freeman Co., San Francisco (1969); Merrifield, J. Am. Chem. Soc., 85 2149 (1963); Meienhofer in "Hormonal Proteins and Peptides," ed.; C. H. Li, Vol. 2 (Academic Press, 1973), pp. 48-267; Bavaay and Merrifield, "The Peptides," eds. E. Gross and F. Meienhofer, Vol. 2 (Academic Press, 1980) pp. 3-285; and Clark-Lewis et al., Meth. Enzymol., 287, 233 (1997). These polypeptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography. The term an "isolated polypeptide" (e.g., an isolated or purified biosynthetic enzyme) is substantially free of cellular material or other contaminating polypeptides from the microorganism from which the polypeptide is derived, or substantially free from chemical precursors or other chemicals when chemically synthesized.

The polypeptides of the invention include polypeptides having amino acid exchanges, i.e., variant polypeptides, so long as the polypeptide variant is biologically active. The variant polypeptides include the exchange of at least one amino acid residue in the polypeptide for another amino acid residue, including exchanges that utilize the D rather than L form, as well as other well known amino acid analogs, e.g., N-alkyl amino acids, lactic acid, and the like. These analogs include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, N-methyl-alanine, para-benzoyl-phenylalanine, phenylglycine, propargylglycine, sarcosine, N-acetylserine, N-formylmethionine, 3-methylhistidine, 5-hydroxylysine, and other similar amino acids and imino acids and tert-butylglycine.

Conservative amino acid exchanges are preferred and include, for example; aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid exchange also includes groupings based on side chains. Members in each group can be exchanged with another. For example, a group of amino acids having aliphatic side chains is glycine, alanine, valine, leucine, and isoleucine. These may be exchanged with one another. A group of amino acids having aliphatic-hydroxyl side chains is serine and threonine. A group of amino acids having amide-containing side chains is asparagine and glutamine. A group of amino acids having aromatic side chains is phenylalanine, tyrosine, and tryptophan. A group of amino acids having basic side chains is lysine, arginine, and histidine. A group of amino acids having sulfur-containing side chains is cysteine and methionine. For example, replacement of a leucine with an isoleucine or valine, an aspartate with a glutamate, a threonine with a serine, or a similar replacement of an amino acid with a structurally related amino acid may be accomplished to produce a variant polypeptide of the invention.

The term "subject" as used herein refers to any animal, including mammals, preferably humans, to which the present invention may be applied.

The term "cancer" or "tumor" refers to an aggregate of abnormal cells and/or tissue which may be associated with diseased states that are characterized by uncontrolled cell proliferation. The disease states may involve a variety of cell types, including, for example, endothelial, epithelial and myocardial cells. Included among the disease states are neoplasms, cancer, leukemia and restenosis injuries.

Beta 1,4 galactosyltransferase

Specific glycosyltransferases synthesize oligosaccharides by the sequential transfer of the monosaccharide moiety of an activated sugar donor to an acceptor molecule. Members of the glycosyltransferase superfamily, which are often named after the sugar moiety that they transfer, are divided into subfamilies on the basis of linkage that is generated between the donor and acceptor. Transfer of the sugar residue occurs with either the retention (by retaining glycosyltransferases) or the inversion (by inverting glycosyltransferases) of the configuration at the anomeric C1 atom.

beta-1,4-Galactosyltransferases (beta4Gal-T) are a Golgi resident, type II membrane-bound family of enzymes (beta4Gal-T1-T7) that transfer galactose (Gal) in the presence of manganese ion (Mn 2+), from UDP-Gal to N-acetylglucosamine (GlcNAc), either free or bound to an oligosaccharide of a glycoprotein or a glycolipid (Brew et al., 1968;

Takase et al., 1984; Powell et al. 1976; Hill, UCLA Forum Med. Sci., 21: 63-86, 1979). This reaction allows galactose to be linked to an N-acetylglucosamine that may itself be linked to a variety of other molecules. Examples of these molecules include other sugars and proteins. The reaction can be used to make many types of molecules of biological significance. For example, galactose-beta (1,4)-N-acetylglucosamine linkages are important for many recognition events that control how cells interact with each other in the body, and how cells interact with pathogens. In addition, numerous other linkages of this type are important for cellular recognition and binding events as well as cellular interactions with pathogens, such as viruses.

Sequences of beta galactosyltransferase I family members from human and other species are known, and family members exhibit a high level of sequence identity in their catalytic domains (Lo et al., 1998; Amado et al., 1998). DNA clones are available from commercial resources, for example, Open Biosources.

Glycosyltransferases show great structural similarity. They are all globular proteins with two types of fold, termed GT-A and GT-B, which each have an N-terminal and a C-terminal domain. The enzymes of the GT-A fold have two dissimilar domains. The N-terminal domain, which recognizes the sugar-nucleotide donor, comprises several b-strands that are each flanked by alpha-helices as in a Rossmann-like fold, whereas the C-terminal domain, which contains the acceptor-binding site, consists largely of mixed b-sheets. By contrast, enzymes with the GT-B fold contain two similar Rossmann-like folds, with the N-terminal domain providing the acceptor-binding site and the C-terminal domain providing the donor-binding site. In both types of enzyme, the two domains are connected by a linker region and the active site is located between the two domains. A metal-binding site is also located in the cleft in enzymes of both the GT-B and GT-A fold (Qasba et al., 2005).

The methods of the invention are amenable to use with any beta 1,4 galactosyltransferase I. By any beta 1,4 galactosyltransferase I is meant from any species, for example, but not limited to, human, bovine, or mouse. Although they have the same donor sugar specificity, many of these are expected to transfer Gal to different oligosaccharides containing GlcNAc at their nonreducing end Although they have the same donor sugar specificity, many of these are expected to transfer Gal to different oligosaccharides containing GlcNAc at their nonreducing end. Recent crystallographic studies on beta4Gal-T1 have provided detailed information about the structure and function of the enzyme (Gastinel et al., 1999; Ramakrishnan et al., 2001; Ramakrishnan et al., 2001a; Ramakrishnan et al., 2002; Ramakrishnan et al., 2002a; Ramakrishnan et al., 2003).

Structural studies on the beta-1,4-galactosyltransferase-1 (beta 4Gal-T1) (Ramikrishnan et al, 2004a) and on other glycosyltransferases (Qasba et al. 2005) have shown that, upon binding the sugar-nucleotide donor substrate, flexible loops at the substrate binding site of these enzymes undergo a marked conformational change, from an open to a closed conformation (Qasba et al. 2005). This change creates an oligosaccharide acceptor-binding site in the enzyme that did not exist before. The loop then acts as a lid covering the bound donor substrate. After the transfer of the glycosyl unit to the acceptor, the saccharide product is ejected, and the loop reverts to its native conformation to release the remaining nucleotide moiety. This conformational change in beta 4Gal-T1 also creates the binding site for beta-lactalbumin, a protein produced in the mammary glands during lactation. The interaction of beta-lactalbumin with beta 4Gal-T1 changes the acceptor specificity of the enzyme from N-acetylglucosamine (GlcNAc) to glucose (Glc), which produces lactose that is secreted in milk. The conformational changes of these two loops are highly coordinated. Trp314 in the small loop plays a crucial role in the conformational state of the long loop, in the binding of the substrates, and in the catalytic mechanism of the enzyme (Ramakrishnan et al, 2001; Gunasekaran et al., 2003). In the unbound state (open conformation), the side chain of Trp is exposed to the solvent (Gastinel et al, 1999; Ramasamy et al. 2003), and the conformation of the long loop is such that the UDP-Gal and the metal binding sites are exposed. Once the substrate binds, the side chain of Trp314 moves into the catalytic pocket to lock the sugar nucleotide in its binding site. Simultaneously, the long loop changes to its closed conformation, masking the sugar nucleotide binding site (Ramakrishnan et al, 2001; Ramakrishnan et al, 2003; Ramasamy et al., 2003). Furthermore, this conformational change in the long flexible loop repositions the amino acid residues at the N-terminal region, creating a metal ion binding site, and at the C-terminal region, creating an oligosaccharide-binding cavity that is also a protein-protein interaction site for R-lactalbumin (LA) (Gasteinel et al., 1999; Ramakrishnan et al, 2001; Ramakrishnan et al, 2003). LA is a mammary gland-specific protein that modulates the acceptor specificity of the enzyme toward glucose (Brodbeck et al., 1967). LA binds at the extended sugar binding site, present only in the closed conformer of beta 4Gal-T1, leaving the monosaccharide binding site of the enzyme available for the binding of Glc or GlcNAc. Since LA competes with the oligosaccharide for binding to the extended sugar binding site (Bell et al, 1976; Powell et al., 1976), it is not possible to crystallize beta 4Gal-T1 in the presence of LA with a bound oligosaccharide acceptor. The wild-type enzyme also does not crystallize in the presence of UDP or UDPhexanolamine, $Mn^{2+}$, and oligosaccharides, thereby restricting our structural or biochemical studies on the interactions of oligosaccharides with beta 4Gal-T1. It has previously been shown that the sugar moiety of the sugar nucleotide is essential for efficiently inducing a conformational change in beta 4Gal-T1 (Geren et al., 1975).

The reaction catalyzed by these enzymes follows a kinetic mechanism in which the metal ion and sugar nucleotide bind to the enzyme first, followed by the acceptor. After the glycosyl moiety of the sugar-nucleotide donor is transferred to the acceptor with the inversion or retention of the C1 configuration, the saccharide product is ejected. The release of the nucleotide and the metal ion follows, which returns the enzyme to its original state for a new round of catalysis.

X-ray crystal structures of the catalytic domain of many glycosyltransferases, either free or bound to substrates, have been determined recently. These studies provide a structural basis for the ordered binding of the donor and acceptor and for the proposed catalytic mechanism of these enzymes (Unligil, U. M. and Rini, J. M. (2000); Berger, E. G. and Rohrer, J; Negishi, M. et al. (2003)).

A three-residue motif, Asp-X-Asp (DXD) or Glu-X-Asp (EXD), or its equivalent generally participates in metal ion binding in enzymes of the GT-A fold. Enzymes of the GT-B fold such as the microbial glycosyltransferases MurG (Hu, Y. et al. (2003)) and GtfB (Mulichack et al. 2001), and BGT (Morera et al. 1999), do not have a DXD motif or its equivalent, even though some, BGT for example, require a metal ion for activity. In glycosyltransferases that require Mn2C ion as cofactor, the metal ion is bound in an octahedral coordination (Qasba et al. 2005). It interacts with one or both acidic residues of the DXD or EXD motif and with two oxygen atoms from the a-phosphate and b-phosphate of UDP. To satisfy the octahedral geometry, the three remaining metal ion links are made either to water molecules or to water in combination with other residues of the protein. In several glycosyltransferases only the first (Lobsanov, Y. D. et al. (2004)) or the second (Gastinel et al. 1999; Ramakrishnan et al. 2001; Ramakrishnan 2002; Unligil 2000) acidic residue of the motif coordinates directly with the metal ion. For example, in some enzymes, the first acidic residue of the motif either interacts directly with the sugar donor or the ribose moiety or interacts via the water molecules coordinated to the Mn2C ion. In blood group A and B and alpha 3GT transferases, by contrast, both aspartic acid residues of the DXD motif directly coordinate the metal ion.

The crystal structures of several glycosyltransferases of either the GT-A or GT-B fold show that at least one flexible loop region has a crucial role in the catalytic mechanism of the enzyme (Qasba et al. 2005). Although the exact location of this loop differs among the transferases, it is invariably located in the vicinity of the sugar nucleotide-binding site. Owing to the flexibility of this region, the loop structure cannot be traced in the apo form of the enzyme, which lacks bound substrate. In the sugar-nucleotide-bound structures, the loop either is in a closed conformation covering the bound donor substrate or is found disordered in the vicinity of the sugar nucleotide-binding site. In a3GT, the C-terminal 11-residue flexible loop changes its conformation when the sugar nucleotide donor is bound (Boix et al., 2001).

Of the six ligands that coordinate Mn2+, three are from bovine beta 4Gal-T1: Asp254, Met344, and His347 (Ramakrishnan et al, 2001; Ramakrishnan et al., 2003; Boeggeman et al., 2002). Residues Met344 and His347, separated by the hinge residue Ile345, are at the N-terminal region of the long flexible loop. The complete metal binding site is created only after His347 has moved during the conformational change to coordinate with the metal ion.

In addition to GlcNAc as an acceptor, the beta-1,4-galactosyltransferase enzyme can also use other sugars, such as N-acyl-substituted glucosamine and N-acetyl-D-mannosamine (Berliner, L. J. et al., Mol. Cell. Biochem., 62: 37-42 (1984)). The beta-1,4-galactosyltransferase does not have an absolute requirement for the sugar donor UDP-Gal; it exhibits polymorphic donor specificity, in that it also transfers glucose (Glc), D-deoxy-Glc, arabinose, GalNAc, and GlcNAc from their UDP derivatives (Berliner, L. J. and Robinson, R. D., Biochemistry, 21: 6340-6343 (1982); Andree, P. J. and Berliner L. J., Biochim. Biophys. Acta, 544: 489-495 (1982); Do, K. Y. et al., J. Biol. Chem., 270: 18477-18451 (1995); Palcic, M. M and Hindsgaul, O., Glycobiology, 1: 205-209 (1991); Ramakrishnan, B. et al., J. Biol. Chem., 276: 37665-37671 (2001)). This reaction can be used to generate many types of molecules, as described herein, which have applications in research and medicine.

Beta 1,4-galactosyltransferase I Doubly Substituted Enzymes

As described herein, residues in the catalytic pocket determine the sugar donor specificities. Substitution of these residues broaden or alter the sugar donor specificities, thus allowing structure-based design of novel glycosyltransferases. A three-residue motif, Asp-X-Asp (DXD) or Glu-X-Asp (EXD), or its equivalent generally participates in metal ion binding in enzymes of the GT-A fold. Enzymes of the GT-B fold such as the microbial glycosyltransferases MurG (Hu, Y. et al. (2003)) and GtfB (Mulichack et al. 2001), and BGT (Morera et al. 1999), do not have a DXD motif or its equivalent, even though some, BGT for example, require a metal ion for activity. In glycosyltransferases that require Mn2C ion as cofactor, the metal ion is bound in an octahedral coordination (Qasba et al. 2005). It interacts with one or both acidic residues of the DXD or EXD motif and with two oxygen atoms from the a-phosphate and b-phosphate of UDP. To satisfy the octahedral geometry, the three remaining metal ion links are made either to water molecules or to water in combination with other residues of the protein. In several glycosyltransferases only the first (Lobsanov, Y. D. et al. (2004)) or the second (Gastinel et al. 1999; Ramakrishnan et al. 2001; Ramakrishnan 2002; Unligil 2000) acidic residue of the motif coordinates directly with the metal ion. For example, in some enzymes, the first acidic residue of the motif either interacts directly with the sugar donor or the ribose moiety or interacts via the water molecules coordinated to the Mn2C ion. In blood group A and B and alpha 3GT transferases, by contrast, both aspartic acid residues of the DXD motif directly coordinate the metal ion.

The crystal structures of several glycosyltransferases of either the GT-A or GT-B fold show that at least one flexible loop region has a crucial role in the catalytic mechanism of the enzyme (Qasba et al. 2005). Although the exact location of this loop differs among the transferases, it is invariably located in the vicinity of the sugar nucleotide-binding site. Owing to the flexibility of this region, the loop structure cannot be traced in the apo form of the enzyme, which lacks bound substrate. In the sugar-nucleotide-bound structures, the loop either is in a closed conformation covering the bound donor substrate or is found disordered in the vicinity of the sugar nucleotide-binding site. In alpha 3GT, the C-terminal 11-residue flexible loop changes its conformation when the sugar nucleotide donor is bound (Boix et al., 2001).

The instant invention describes catalytic domains of beta 1,4-galactosyltransferase I with amino acid exchanges.

The instant invention describes catalytic domains of beta 1,4-galactosyltransferase I with amino acid substitutions or exchanges. FIG. 6 shows the nucleotide sequence corresponding to human beta 1,4 galactosyltransferase-I (SEQ ID NO: 5) according to NCBI Accession No. NM_001005417, and FIG. 7 shows the amino acid sequence corresponding to human beta 1,4 galactosyltransferase-I (SEQ ID NO: 6) according to NCBI Accession No. NM_001005417. One of skill in the art using the guidance provided herein can make amino acid substitutions or exchanges at residues of beta 1,4-galactosyltransferase I that broaden or alter donor specificity.

In certain examples, the amino acid exchange is an amino acid at positions 285 and 340, corresponding to human beta 1,4-galactosyltransferase I. In other certain examples, the amino acid exchange is an amino acid at positions 289 and 344 corresponding to bovine beta 1,4-galactosyltransferase I (see, for example, PCT/US2004/000470 and US Application No. 20060084162, both of which are incorporated herein by reference in their entireties). The corresponding tyrosine in the mouse beta 1,4-galactosyltransferase I is located at amino acid position 286. Other examples of specific exchanges are Y289I and Y289N, corresponding to Y285I and Y285N in human.

Those of skill in the art can readily determine equivalent amino acids in other beta 1,4-galactosyltransferase I catalytic domains and generate them through recombinant techniques known in the art.

Included in the invention are polypeptide fragments from a beta (1,4)-galactosyltransferase I that transfers GalNAc or galactose from a sugar donor to a sugar acceptor in the presence of magnesium. In certain examples, the catalytic domain comprises an amino acid exchange at amino acid positions 285 and 340 corresponding to human beta (1,4)-galactosyltransferase I. In other examples, the catalytic domain comprises a conservative amino acid exchange at amino acid positions 289 and 344 corresponding to bovine beta (1,4)-galactosyltransferase I.

In the human sequence of the enzyme, the Leucine (L) can be exchanged for a tyrosine (Y) at amino acid position 285 and a methionine (M) is exchanged for a histidine (H) at amino acid position 340. In the bovine sequence of the enzyme, a leucine (L) is exchanged for a tyrosine (Y) at amino acid position 289 and a methionine (M) is exchanged for a histidine (H) at amino acid position 344.

In preferred examples, the invention features a polypeptide fragment from a beta (1,4)-galactosyltransferase I that transfers GalNAc or galactose from a sugar donor to a sugar acceptor, wherein the isolated catalytic domain comprises SEQ ID NO: 1.

In certain preferred embodiments of the invention, the catalytic domain corresponds to amino acids 127-398 of the doubly substituted mutant human beta-4Gal-T1-M340H-Y285L. SEQ ID NO: 1 represents the DNA sequence corresponding to the protein sequence, amino acid residues 127 to 398:

A number of sugar donors are available, and are selected from UDP-GalNAc, UDP-GalNAc analogues, UDP-galactose, or UDP-galactose analogues. The UDP-GalNAc analogues or UDP-galactose analogue can comprise an azido group, a keto group, or a thiol group. In order to link an agent to the UDP-galactose analogue, the azido group, the keto group or the thiol group is substituted at the C2 position of galactose. The invention enables a range of agents to be linked to the sugar moiety of the sugar donor. For instance, the agent can be selected from antibodies, single chain antibodies, bacterial toxins, growth factors, therapeutic agents, targeting agents, contrast agents, chemical labels, a radiolabels, and fluorescent labels.

The sugar acceptor is preferably N-acetylglucosamine (GlcNAc). The N-acetylglucosamine (GlcNAc) can free or attached to a peptide of a glycopeptide.

Flexible loops undergo conformational changes upon substrate binding and create the acceptor binding site and the catalytic pocket. Metal ions often bind at the hinge region of the flexible loop. Since 5 mM $Mn^{2+}$ is toxic to live cells, the

```
                                                         (SEQ ID NO: 1)
  1  CTGCCCGCAT GCCCTGAGGA GTCCCCGCTG CTTGTGGGCC CCATGCTGAT

51  TGAGTTTAAC ATGCCTGTGG ACCTGGAGCT CGTGGCAAAG CAGAACCCAA

101  ATGTGAAGAT GGGCGGCCGC TATGCCCCCA GGGACTGCGT CTCTCCTCAC

151  AAGGTGGCCA TCATCATTCC ATTCCGCAAC CGGCAGGAGC ACCTCAAGTA

201  CTGGCTATAT TATTTGCACC CAGTCCTGCA GCGCCAGCAG CTGGACTATG

251  GCATCTATGT TATCAACCAG GCGGGAGACA CTATATTCAA TCGTGCTAAG

301  CTCCTCAATG TTGGCTTTCA AGAAGCCTTG AAGGACTATG ACTACACCTG

351  CTTTGTGTTT AGTGACGTGG ACCTCATTCC AATGAATGAC CATAATGCGT

401  ACAGGTGTTT TCACAGCCA CGGCACATTT CCGTTGCAAT GGATAAGTTT

451  GGATTCAGCC TACCTTATGT TCAGTTGTTT GGAGGTGTCT CTGCTCTAAG

501  TAAACAACAG TTTCTAACCA TCAATGGATT TCCTAATAAT TATTGGGGCT

551  GGGGAGGAGA AGATGATGAC ATTTTTAACA GATTAGTTTT TAGAGGCATG

601  TCTATATCTC GCCCAAATGC TGTGGTCGGG AGGACGCGTC ACATCCGCCA

651  CTCGAGAGAC AAGAAAAATG AACCCAATCC TCAGAGGTTT GACCGAATTG

701  CACACACAAA GGAGACAATG CTCTCTAATG GTTTGAACTC ACTCACCTAC

751  CAGGTGCTGG ATGTACAGAG ATACCCATTG TATACCCAAA TCACAGTGGA

801  CATCGGGACA CCGAGCTAG
```

SEQ ID NO: 2 represents the protein sequence corresponding to amino acid residues 127 to 398:

$Mg^{2+}$ dependent b4Gal-Y285L M340H-Gal-T1 double mutant, is a better choice for the galactosylation of live cells.

```
                                                         (SEQ ID NO: 2)
127  LPACPEESPL LVGPMLIEFN MPVDLELVAK QNPNVKMGGR YAPRDCVSPH

177  KVAIIIPFRN RQEHLKYWLY YLHPVLQRQQ LDYGIYVINQ AGDTIFNRAK

227  LLNVGFQEAL KDYDYTCFVF SDVDLIPMND HNAYRCFSQP RHISVAMDKF

277  GFSLPYVQLF GGVSALSKQQ FLTINGFPNN YWGWGGEDDD IFNRLVFRGM

327  SISRPNAVVG RTRHIRHSRD KKNEPNPQRF DRIAHTKETM LSNGLNSLTY

377  QVLDVQRYPL YTQITVDIGT PS*
```

The sugar transfer of the instant invention is unique in that in preferred embodiments sugar transfer occurs in the presence of magnesium.

Nucleic Acids and Vectors

The present invention provides isolated nucleic acid segments that encode catalytic domains of double mutant beta 1,4 galactosyltransferase, for example in certain embodiments human beta-1,4-Tyr285Leu-Met340His-Gal-T1. Nucleic acid sequences encoding a double mutant beta 1,4 galactosyltransferase, human beta-1,4-Tyr285Leu-Met340His-Gal-T1, for example SEQ ID NO: 1, as well as other beta 1,4 galactosyltransferases from other organisms are available. These nucleic acid sequences can be modified to encode the polypeptide fragments and amino acid segments of the invention through use of well-known techniques (Sambrook et al., Molecular Cloning: A Laboratory Manual, 3rd edition, Cold Spring Harbor Press, Cold Spring Harbor, N.Y. (2001)). For example, a portion of the nucleic acid sequence encoding beta 1,4 galactosyltransferase, for example SEQ ID NO: 1, can be inserted into an expression vector such that an amino acid segment corresponding to the catalytic domain of the double mutant beta 1,4 galactosyltransferase, human beta-1,4-Tyr285Leu-Met340His-Gal-T1 (SEQ ID NO: 2) is expressed upon transformation of a cell with the expression vector. The nucleic acid segments of the invention may be optimized for expression in select cells. Codon optimization tables are available. Harlow and Lane, Antibodies: A Laboratory Manual, Cold Spring Harbor Laboratory Press, 1988.

The nucleic acid segments can be inserted into numerous types of vectors. A vector may include, but is not limited to, any plasmid, phagemid, F-factor, virus, cosmid, or phage in double or single stranded linear or circular form, which may or may not be self-transmissible or mobilizable. The vector can also transform a prokaryotic or eukaryotic host either by integration into the cellular genome or exist extrachromosomally (e.g. autonomous replicating plasmid with an origin of replication).

Preferably the nucleic acid segment in the vector is under the control of, and operably linked to, an appropriate promoter or other regulatory elements for transcription in vitro or in a host cell such as a eukaryotic cell or microbe, e.g. bacteria. The vector may be a bi-functional expression vector which functions in multiple hosts. In the case of genomic DNA, this may contain its own promoter or other regulatory elements and in the case of cDNA this may be under the control of a promoter or other regulatory sequences for expression in a host cell.

Specifically included are shuttle vectors by which is meant a DNA vehicle capable, naturally or by design, of replication in two different host organisms, which may be selected from bacteria and eukaryotic cells (e.g. mammalian, yeast or fungal).

The vector may also be a cloning vector which typically contains one or a small number of restriction endonuclease recognition sites at which nucleic acid segments can be inserted in a determinable fashion. Such insertion can occur without loss of essential biological function of the cloning vector. A cloning vector may also contain a marker gene that is suitable for use in the identification and selection of cells transformed with the cloning vector. Examples of marker genes are tetracycline resistance, hygromycin resistance or ampicillin resistance. Many cloning vectors are commercially available (Stratagene, New England Biolabs, Clonetech).

The nucleic acid segments of the invention may also be inserted into an expression vector. Typically an expression vector contains (1) prokaryotic DNA elements coding for a bacterial replication origin and an antibiotic resistance gene to provide for the amplification and selection of the expression vector in a bacterial host; (2) regulatory elements that control initiation of transcription such as a promoter; and (3) DNA elements that control the processing of transcripts such as introns, transcription termination/polyadenylation sequence.

Methods to introduce a nucleic acid segment into a vector are well known in the art (Sambrook et al., 1989). Briefly, a vector into which the nucleic acid segment is to be inserted is treated with one or more restriction enzymes (restriction endonuclease) to produce a linearized vector having a blunt end, a "sticky" end with a 5' or a 3' overhang, or any combination of the above. The vector may also be treated with a restriction enzyme and subsequently treated with another modifying enzyme, such as a polymerase, an exonuclease, a phosphatase or a kinase, to create a linearized vector that has characteristics useful for ligation of a nucleic acid segment into the vector. The nucleic acid segment that is to be inserted into the vector is treated with one or more restriction enzymes to create a linearized segment having a blunt end, a "sticky" end with a 5' or a 3' overhang, or any combination of the above. The nucleic acid segment may also be treated with a restriction enzyme and subsequently treated with another DNA modifying enzyme. Such DNA modifying enzymes include, but are not limited to, polymerase, exonuclease, phosphatase or a kinase, to create a polynucleic acid segment that has characteristics useful for ligation of a nucleic acid segment into the vector.

The treated vector and nucleic acid segment are then ligated together to form a construct containing a nucleic acid segment according to methods known in the art (Sambrook, 2002). Briefly, the treated nucleic acid fragment and the treated vector are combined in the presence of a suitable buffer and ligase. The mixture is then incubated under appropriate conditions to allow the ligase to ligate the nucleic acid fragment into the vector. It is preferred that the nucleic acid fragment and the vector each have complimentary "sticky" ends to increase ligation efficiency, as opposed to blunt-end ligation. It is more preferred that the vector and nucleic acid fragment are each treated with two different restriction enzymes to produce two different complimentary "sticky" ends. This allows for directional ligation of the nucleic acid fragment into the vector, increases ligation efficiency and avoids ligation of the ends of the vector to reform the vector without the inserted nucleic acid fragment.

Suitable prokaryotic vectors include but are not limited to pBR322, pMB9, pUC, lambda bacteriophage, m13 bacteriophage, and Bluescript®. Suitable eukaryotic vectors include but are not limited to PMSG, pAV009/A+, PMTO10/A+, pMAM neo-5, bacculovirus, pDSVE, YIPS, YRP17, YEP. It will be clear to one of ordinary skill in the art which vector or promoter system should be used depending on which cell type is used for a host cell.

The invention also provides expression cassettes which contain a control sequence capable of directing expression of a particular nucleic acid segment of the invention either in vitro or in a host cell. The expression cassette is an isolatable unit such that the expression cassette may be in linear form and functional in in vitro transcription and translation assays. The materials and procedures to conduct these assays are commercially available from Promega Corp. (Madison, Wis.). For example, an in vitro transcript may be produced by placing a nucleic acid segment under the control of a T7 promoter and then using T7 RNA polymerase to produce an in vitro transcript. This transcript may then be translated in vitro through use of a rabbit reticulocyte lysate. Alternatively, the expression cassette can be incorporated into a vector allowing for replication and amplification of the expression cassette within a host cell or also in vitro transcription and translation of a nucleic acid segment.

Such an expression cassette may contain one or a plurality of restriction sites allowing for placement of the nucleic acid segment under the regulation of a regulatory sequence. The expression cassette can also contain a termination signal operably linked to the nucleic acid segment as well as regulatory sequences required for proper translation of the nucleic acid segment. Expression of the nucleic acid segment in the expression cassette may be under the control of a constitutive promoter or an inducible promoter, which initiates transcription only when the host cell is exposed to some particular external stimulus.

The expression cassette may include in the 5'-3' direction of transcription, a transcriptional and translational initiation region, a nucleic acid segment and a transcriptional and translational termination region functional in vivo and/or in vitro. The termination region may be native with the transcriptional initiation region, may be native with the nucleic acid segment, or may be derived from another source. Numerous termination regions are known in the art. Guerineau et al., Mol. Gen. Genet., 262:141 (1991); Proudfoot, Cell, 64:671 (1991); Sanfacon et al., Genes Dev., 5:141 (1991); Munroe et al., Gene, 91:151 (1990); Ballas et al., Nucleic Acids Res., 17:7891 (1989); Joshi et al., Nucleic Acid Res., 15:9627 (1987).

The regulatory sequence can be a nucleic acid sequence located upstream (5' non-coding sequences), within, or downstream (3' non-coding sequences) of a coding sequence, and which influences the transcription, RNA processing or stability, or translation of the associated coding sequence. Regulatory sequences can include, but are not limited to, enhancers, promoter and repressor binding sites, translation leader sequences, introns, and polyadenylation signal sequences. They may include natural and synthetic sequences as well as sequences that may be a combination of synthetic and natural sequences. While regulatory sequences are not limited to promoters, some useful regulatory sequences include constitutive promoters, inducible promoters, regulated promoters, tissue-specific promoters, viral promoters and synthetic promoters.

A promoter is a nucleotide sequence that controls expression of the coding sequence by providing the recognition for RNA polymerase and other factors required for proper transcription. A promoter includes a minimal promoter, consisting only of all basal elements needed for transcription initiation, such as a TATA-box and/or initiator that is a short DNA sequence comprised of a TATA-box and other sequences that serve to specify the site of transcription initiation, to which regulatory elements are added for control of expression. A promoter may be inducible. Several inducible promoters have been reported (Current Opinion in Biotechnology, 7:168 (1996)). Examples include the tetracycline repressor system, Lac repressor system, copper-inducible systems, salicylate-inducible systems (such as the PR1a system). Also included are the benzene sulphonamide (U.S. Pat. No. 5,364,780, incorporated by reference herein) and alcohol- (WO 97/06269 and WO 97/06268, both incorporated by reference herein) inducible systems and glutathione S-transferase promoters. In the case of a multicellular organism, the promoter can also be specific to a particular tissue or organ or stage of development.

An enhancer is a DNA sequence which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects.

The expression cassette can contain a 5' non-coding sequence which is a nucleotide sequence located 5' (upstream) to the coding sequence. It is present in the fully processed mRNA upstream of the initiation codon and may affect processing of the primary transcript to mRNA, stability of the mRNA, or translation efficiency (Turner et al., Molecular Biotechnology, 3:225 (1995)).

The expression cassette may also contain a 3' non-coding sequence, which is a nucleotide sequence, located 3' (downstream) to a coding sequence and includes polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The invention also provides a construct containing a vector and an expression cassette. The vector may be selected from, but not limited to, any vector previously described. Into this vector may be inserted an expression cassette through methods known in the art and previously described (Sambrook et al., 1989). In one embodiment, the regulatory sequences of the expression cassette may be derived from a source other than the vector into which the expression cassette is inserted. In another embodiment, a construct containing a vector and an expression cassette is formed upon insertion of a nucleic acid segment of the invention into a vector that itself contains regulatory sequences. Thus, an expression cassette is formed upon insertion of the nucleic acid segment into the vector. Vectors containing regulatory sequences are available commercially and methods for their use are known in the art (Clonetech, Promega, Stratagene).

The expression cassette, or a vector construct containing the expression cassette may be inserted into a cell. The expression cassette or vector construct may be carried episomal or integrated into the genome of the cell.

A variety of techniques are available and known to those skilled in the art for introduction of constructs into a cellular host. Transformation of bacteria and many eukaryotic cells may be accomplished through use of polyethylene glycol, calcium chloride, viral infection, phage infection, electroporation and other methods known in the art. Other transformation methods are available to those skilled in the art, such as direct uptake of foreign DNA constructs (see EP 295959, incorporated by reference herein), techniques of electroporation or high velocity ballistic bombardment with metal particles coated with the nucleic acid constructs (U.S. Pat. No. 4,945,050, incorporated by reference herein).

The selection of an appropriate expression vector will depend upon the method of introducing the expression vector into host cells. Typically an expression vector contains (1) prokaryotic DNA elements coding for a bacterial origin of replication and an antibiotic resistance gene to provide for the amplification and selection of the expression vector in a bacterial host; (2) DNA elements that control initiation of transcription, such as a promoter; (3) DNA elements that control the processing of transcripts, such as introns, transcription termination/polyadenylation sequence; and (4) a reporter gene that is operatively linked to the DNA elements to control transcription initiation. Useful reporter genes include beta-galactosidase, chloramphenicol acetyl transferase, luciferase, green fluorescent protein (GFP) and the like.

Methods of Making and Folding

Galactosyltransferase enzymes of the invention may be produced in soluble form. Methods that may be used to produce such soluble enzymes have been described (U.S. Pat. No. 5,032,519, incorporated by reference in its entirety herein). Briefly, a hydrophobic transmembrane anchor region of a galactosyltransferase is removed to produce an enzyme that is in soluble form.

Alternatively, 1,4 beta galactosyltransferase enzymes of the invention may be produced such that they are anchored in the membrane of a cell. Such enzymes may be produced that are anchored in the membranes of prokaryotic and eukaryotic cells. Methods to produce such enzymes have been described (U.S. Pat. No. 6,284,493, incorporated by reference in its entirety herein).

Briefly, in the case of procaryotes, the signal and transmembrane sequences of the transferase, for example the mutant 1,4 beta galactosyltransferase of the invention, are replaced by a bacterial signal sequence, capable of effecting localization of the fusion protein to the outer membrane. Suitable signal sequences include, but are not limited to those from the major E. coli lipoprotein Lpp and lam B. In addition, membrane spanning regions from Omp A, Omp C, Omp F or Pho E can be used in a tripartite fusion protein to direct proper insertion of the fusion protein into the outer membrane. Any prokaryotic cells can be used in accordance with the present invention including but not limited to E. coli, Bacillus sp., and Pseudomonas sp. as representative examples.

It is also possible, in certain embodiments, that the native transmembrane domain of the glycosyltransferase, for example the engineered 1,4 beta galactosyltransferase of the invention as described herein, is replaced by the transmembrane domain of a bacterial outer membrane protein. For example, the 1,4 beta galactosyltransferase signal sequence and the bacterial transmembrane region act in concert to anchor the galactosyltransferase to the bacterial outer cell membrane. Nearly any outer membrane bound protein is suitable for this use including but not limited to Omp A, Omp C, and Omp F, Lpp, and Lam B. The catalytic portion of the 1,4 beta galactosyltransferase should be fused to an extracellular loop in the bacterial transmembrane region in order to insure proper orientation of the fusion protein on the outer membrane surface and not in the cytoplasm or periplasm of the cell. Insertion of a protein into such a loop region has been previously reported (Charbit et al., J. Bacteriology, 173:262 (1991); Francisco et al., Proc. Natl. Acad. Sci., 89:2713 (1992)).

The present invention is also applicable for use with eukaryotic cells resulting in cell surface expression of glycosyltransferases in known culturable eukaryotic cells including but not limited to yeast cells, insect cells, chinese hamster ovary cells (CHO cells), mouse L cells, mouse A9 cells, baby hamster kidney cells, C127 cells, COS cells, Sf9 cells, and PC8 cells.

In another example of the present invention, the transmembrane domain of the glycosyltransferase is replaced by the transmembrane domain of a plasma membrane protein. The transmembrane domain of any resident plasma membrane protein will be appropriate for this purpose. For example, but not to be limiting, the transmembrane portions of the M6 P/IGF-II receptor, LDL receptor or the transferrin receptor are representative examples.

In another embodiment the Golgi retention signal of the glycosyltransferase is disrupted by site-directed mutagenesis. This approach mutates the amino acids responsible for localizing the galactosyltransferase to the Golgi compartment. The resultant glycosyltransferase is transported to the plasma membrane where it becomes anchored via its modified transmembrane sequences.

In vitro folding of 1,4 beta galactosyltransferase requires proper disulfide bond formation. Ways to ensure proper disulfide bond formation include S-sulfonation of the protein prior to disulfide formation, use of oxido-shuffling reagents, and mutation of free Cys residue to Thr. In the in vitro folding of beta4GalT1, the stem region acts as a chaperone. Additionally, there are additives that can be used to prevent the hydrophobic collapse, including polyethylene glycol (PEG, e.g. PEG-4000) or L-arginine-HCl. PEG-4000 and L-arginine are thought to beneficially affect the solubility of folding intermediates of both catalytic domain-proteins (CD-proteins) and stem region/catalytic domain proteins (SRCD-proteins) during in vitro folding or protein obtained from inclusion bodies. In the case of catalytic domain (CD)-proteins, the majority of misfolded proteins are insoluble in the absence of PEG-4000 and L-arginine and so they precipitate out during dialysis. Thus, the process will leave behind the properly folded molecules in solution bound to UDP-agarose that are enzymatically active.

Beta (1,4)-galactosyltransferase I is a type II Golgi resident protein with a short cytoplasmic tail, a transmembrane domain followed by a stem region and has a globular catalytic domain that faces the Golgi lumen. When the catalytic domain of beta (1,4)-galactosyltransferase I is expressed in E. Coli, it forms insoluble inclusion bodies. General methods for isolating and folding inclusion bodies containing galactosyltransferase catalytic domains have been previously described (Ramakrishnan et al., J. Biol. Chem., 276:37665 (2001)). These inclusion bodies can be collected and then solubilized and folded in vitro to produce catalytically active domains. Thus, the in vitro folding efficiency is directly related to the quantity of active enzyme that is produced from the isolated inclusion bodies. Accordingly, methods to increase the in vitro folding efficiency would provide increased production of catalytic domains that can be used to create useful products. US Application 20060084162, incorporated by reference in its entirety herein, provides materials and methods that improve in vitro folding of catalytic domains from galactosyltransferases that are related to the use of a stem region of beta (1,4)-galactosyltransferase I. Such methods are of use in the instant invention.

Methods of the Invention

The methods as described herein provide the ability to conjugate multiple agents to compounds or compositions of the invention. An embodiment of the present invention provides a glycoconjugate in which one or more bioactive agents are bound to a modified saccharide (e.g. a sugar) residue, for example, a modified galactose, which is in turn bound to a targeting compound, e.g., a compound capable of binding a receptor on a cell membrane. In this manner, many targeting glycoconjugates can be constructed. An example, not meant to be limiting, is a gene delivery system for genetic therapy that can be produced by binding a nucleotide and a ligand or antibody to the modified sugar. A therapeutic compound for cancer can be produced by binding a chemotherapeutic agent and a ligand or antibody, e.g., an antibody to a cancer antigen, to the modified sugar residue.

The glycoconjugates can be manufactured as designer glycoconjugates, according to therapeutic need. As such, the designer polypeptide itself can be used for the targeting and drug delivery. The glycoconjugates can be manufactured as nanoparticles. In certain examples, a biological substrate, such as a bioactive agent, for example a therapeutic agent, is used to engineer the nanoparticle. In other examples a second, third, fourth or more bioactive polypeptide is used in association with the nanoparticle to engineer multivalent nanoparticles. The bioactive agents do not have to be the same, for example a nanoparticle comprising three bioactive agents may comprise a chemotherapeutic, a tracking agent and a targeted delivery agent, such as an antibody.

The glycoconjugates can be manufactured according to the methods described herein can be nanoparticles. Nanoparticles of the invention have use in methods of treating diseases.

In other examples, the methods of the invention are used to engineer a glycoprotein from a magnetic resonance agent for use in diagnostic therapies. In these preferred examples, nanoparticles are engineered as described herein, where the nanoparticles are superparamagnetic nanoparticle.

Catalytic domains of the invention having altered donor and acceptor specificity can be used to catalyze the linkage of numerous sugars from a donor to numerous acceptor sugars. Linkage of sugar derivatives can also achieved through use of the altered catalytic domains of the invention due to their expanded donor and acceptor specificity.

The presence of modified sugar moieties on a glycoprotein makes it possible to link bioactive molecules via modified glycan chains, thereby assisting in the assembly of bionanoparticles that are useful for developing the targeted drug delivery system and contrast agents for example for use in imaging, e.g., magnetic resonance imaging. The reengineered recombinant glycosyltransferases as described herein also make it possible to remodel the oligosaccharide chains of glycoprotein drugs, and to synthesize oligosaccharides for vaccine development.

Targeted Glycoconjugates

Beta 1,4-galactosyltransferase (GalT) catalyzes the transfer of galactose from the donor UDP-galactose, to an acceptor, N-acetylglucosamine (GlcNAc, present at the non-reducing terminal end of glycans of glycoproteins and glycolipids, to form a galactose-beta-1,4-N-acetylglucosamine bond (Hill, UCLA Forum Med. Sci., 21: 63-86 (1979). This reaction allows galactose to be linked to an N-acetylglucosamine that may itself be linked to a variety of other molecules, such as sugars and proteins, e.g., antibodies. In addition to GlcNAc as an acceptor, the enzyme can also use other sugars, such as N-acyl-substituted glucosamine and N-acetyl-D-mannosamine (Berliner, L. J. et al., Mol. Cell. Biochem., 62: 37-42 (1984)). The enzyme does not have an absolute requirement for the sugar donor UDP-Gal; instead, it exhibits polymorphic donor specificity, in that it also transfers glucose (Glc), D-deoxy-Glc, arabinose, GalNAc, and GlcNAc from their UDP derivatives (Berliner, L. J. and Robinson, R. D., Biochemistry, 21: 6340-6343 (1982); Andree, P. J. and Berliner L. J., Biochim. Biophys. Acta, 544: 489-495 (1982); Do, K. Y. et al., J. Biol. Chem., 270: 18477-18451 (1995); Palcic, M. M and Hindsgaul, O., Glycobiology, 1: 205-209 (1991); Ramakrishnan, B. et al., J. Biol. Chem., 276: 37665-37671 (2001)). This reaction can be used to generate many types of molecules, as described herein, which have applications in research and medicine.

As described herein, modifications in sugar donors, for example UDP-GalNAc analogues or UDP-galactose analogues, are tolerated by the beta 1,4 galactosyltransferase mutants. The beta 1,4 galT mutants of the invention have the ability to use unnatural substrates, due to altered donor specificity, in sugar transfer reactions. For example, in one embodiment, the catalytic domain of GalT has a tyrosine exchanged with another amino acid at an amino acid position corresponding to 289 in the bovine beta (1,4)-galactosyltransferase I (see, for example, PCT/US2004/000470, filed Jan. 9, 2004, which is incorporated herein by reference) and a tyrosine exchanged with another amino acid at an amino acid position corresponding to 285 in the human beta (1,4)-galactosyltransferase I.

One of skill in the art can readily determine equivalent amino acids in other (1,4)-galactosyltransferase I catalytic domains and generate amino acid exchanges through recombinant techniques known in the art. In one embodiment, a genetically engineered form of beta (1,4)-galactosyltransferase I that transfers GalNAc or galactose from a sugar donor to a sugar acceptor glycol-polypeptide in the presence of magnesium is used to catalyze the formation of the glycoconjugates of the invention. This genetically engineered form of beta 1,4 GalT has an enlarged binding pocket which enhances the catalytic activity toward GalNAc substrates without compromising specificity (See, Khidekel et al., 2003 and PCT/US04/00470, filed Jan. 9, 2004, both of which are incorporated herein by reference).

In one embodiment of the invention, the donor sugar is modified so as to include a functional group at the C2 position of the sugar ring, preferably a ketone or an azido or a thiol functionality. In another embodiment, the modified sugar is a galactose or a GalNAc analogue, which is modified at the C2 position by the addition of ketone functionality.

WO 2005/051429, incorporated by reference in its entirety herein, describes methods used to bind a bioactive agent to the modified sugar. The bioactive compounds may preferably include a functional group which may be useful, for example, in forming covalent bonds with the sugar residue, which are not generally critical for the activity of the bioactive agent. Examples of such functional groups include, for example, amino(—NH: 2), hydroxy(—OH), carboxyl (—COOH), thiol (—SH), phosphate, phosphinate, ketone group, sulfate and sulfinate groups. If the bioactive compounds do not contain a useful group, one can be added to the bioactive compound by, for example, chemical synthetic means. Where necessary and/or desired, certain moieties on the components may be protected using blocking groups, as is known in the art, see, e.g., Green & Wuts, Protective Groups in Organic Synthesis (John Wiley & Sons) (1991).

Exemplary covalent bonds by which the bioactive compounds may be associated with the sugar residue include, for example, amide (—CONH—); thioamide (—CSNH—); ether (ROR', where R and R' may be the same or different and are other than hydrogen); ester (—COO—); thioester (—COS—); —O—; —S—; —Sn—, where n is greater than 1, preferably about 2 to about 8; carbamates; —NH—; —NR—, where R is alkyl, for example, alkyl of from about 1 to about 4 carbons; urethane; and substituted imidate; and combinations of two or more of these.

Covalent bonds between a bioactive agent and a modified sugar residue may be achieved through the use of molecules that may act, for example, as spacers to increase the conformational and topographical flexibility of the compound. Examples of such spacers include, for example, succinic acid, 1,6-hexanedioic acid, 1,8-octanedioic acid, and the like, as well as modified amino acids, such as, for example, 6-aminohexanoic acid, 4-aminobutanoic acid, and the like.

One of skill in the art can easily chose suitable compatible reactive groups for the bioactive agent and the modified sugar, so as to generate a covalent bond between the bioactive agent and the modified sugar. Also, while the glycoconjugates of the invention are generally described with the targeting agent as the acceptor molecule or structure onto which a donor molecule (e.g., UDP-galactose) is actively linked through the action of a catalytic domain of a galactosyltransferase, or mutant thereof, the bioactive agent can also be an acceptor molecule.

In certain embodiments, the instant method can be used to monitor glycosylation, for example the glycosylation of therapeutic glycoproteins and monoclonal antibodies. The potential of glycosyltransferase mutants to produce glycoconjugates carrying sugar moieties with reactive groups may be a benefit to the glycotargeting of drugs to their site of action. Although a great number of pharmaceutical agents are discovered each year, the clinical application of these is many times hindered because of failure to reach the site of action. The methods described herein that include using mutant glycosyltransferases to transfer chemically reactive sugar residues for linking of other molecules via specific glycan chains may be used as an efficient drug delivery system.

Detection

The beta (1,4) glycosyltransferases as described herein have application in the detection of specific sugar residues on a glycan chain of a glycoconjugates and in the glycoconjugation and assembly of bio-nanoparticles for the targeted delivery of bioactive agents. Protein glycoslation is one of the most abundant posttranslational modifications and plays a fundamental role in the control of biological systems and in disease. The O-GlcNAc modification on proteins is the dynamic posttranslational modification in which the beta-N-acetylglucosamine is covalently attached to serine or threonine residues in proteins.

Accordingly, glycosylation has been found to be a marker in disease. For example, in cancer, tumor beta-1,4-galactosyltransferase IV overexpression is closely associated with colorectal cancer metastasis and poor prognosis. Chen W S et al. Clin Cancer Res. 2005 Dec. 15; 11(24 Pt 1):8615-22). Further, carbohydrate modifications have been shown to be important for host-pathogen interactions, inflammation, development, and malignancy (Varki, 1993; Lasky, 1996;).

Several methods have been reported for the identification of O-GlcNAc modification on proteins. One of the detection methods involves the enzymatic labeling by beta 4Gal-T1 of O-GlcNAc using UDP-3H galactose; however, this method is time-consuming and expensive.

The methods described herein offer the advantages the modification occurs in a site directed manner, only where the carbohydrate is attached to the glycoprotein. Such specificity permits, for example, the use of site-directed immunotherapy without affecting the antigen binding affinity of the immunoglobulin. Such specificity permits, further, the potential use of this approach in developing a drug delivery system or biological probes.

Imaging

Included in the invention are methods for imaging a target cell or tissue in a subject. The methods as described herein comprise administering to a subject a polypeptide fragment synthesized by the method comprising incubating a reaction mixture comprising a polypeptide fragment from a beta (1,4)-galactosyltransferase I with a sugar donor, wherein one or more imaging agents are linked to the sugar donor, and an sugar acceptor thereby imaging a target cell or tissue. The polypeptide fragment can comprise an amino acid exchange at amino acid positions 285 and 340 corresponding to human beta (1,4)-galactosyltransferase I. The polypeptide fragment can comprise a conservative amino acid exchange at amino acid positions 289 and 344 corresponding to bovine beta (1,4)-galactosyltransferase I. In some examples, a leucine (L) is exchanged for a tyrosine (Y) at amino acid position 285 and a methionine (M) is exchanged for a histidine (H) at amino acid position 340. In other examples, a leucine (L) is exchanged for a tyrosine (Y) at amino acid position 289 and a methionine (M) is exchanged for a histidine (H) at amino acid position 344.

In preferred examples, the sugar donor is a UDP-galactose analogue that comprises an azido group, a keto group, or a thiol group that is substituted at the C2 position of galactose. The imaging agents are linked to a sugar moiety of the sugar donor.

An imaging agent can be used according to the diagnostic or therapeutic use as desired. For example, the imaging agent can be selected from the group consisting of: chemical labels, radiolabels, and fluorescent labels.

The sugar acceptor is N-acetylglucosamine (GlcNAc), and the N-acetylglucosamine (GlcNAc) is free or attached to a peptide of a glycopeptide.

In the imaging methods as described herein, the isolated catalytic domain comprises SEQ ID NO: 1. The methods can take place in the presence of magnesium.

Coupling

Methods of transfer of C2 modified galactose analogues, for example C2 keto galactose from its UDP derivative to the GlcNAc residue on the N-glycan chain of ovalbumin or to an asialo-agalacto-IgG1 molecule have been described in the art, for example in WO 2005/051429, incorporated by reference in its entirety herein. The C2 modified galactose analogues, for example C2 keto galactose can be biotinylated, thus allowing for biotinylation of carriers such as ovalbumin and IgG. Methods for transfer of by beta4 Gal-T1 enzyme have been described in the art (Boeggeman, et al 2007).

The method of coupling a target agent to a carrier protein via glycan chains, for example ovalbumin and IgG1, is advantageous over other cross-linking methods. In the instant method, the target agent is linked in a site-directed manner, only where the carbohydrate is attached to the glycoprotein, for example as in the IgG1 molecule at the Fc domain, away from the antigen binding site. A problem encountered in previous approaches using monoclonal antibodies for immunotherapy is the lack of specificity of the reactions, resulting in heterologous labeling and a decrease in the antibody affinity for the antigen. The instant invention overcomes this problem.

Accordingly, the invention features methods of coupling an agent or agents to a carrier protein. The methods as described herein comprise incubating a reaction mixture comprising a polypeptide fragment from a beta (1,4)-galactosyltransferase I, wherein the polypeptide fragment comprises SEQ ID NO: 1, with a sugar donor, and a carrier protein, in the presence of magnesium.

The sugar donor is, in certain examples, a UDP-galactose analogue or a UDP-GalNAc analogue that can comprise an azido group, a keto group, or a thiol group. The azido group, the keto group or the thiol group can be substituted at the C2 position of galactose, thus allowing for linking of agents. Accordingly, in certain preferred examples, one or more agents are linked to a sugar moiety of the sugar donor. The agent can be selected from the group consisting of: antibodies, single chain antibodies, bacterial toxins, growth factors, therapeutic agents, targeting agents, contrast agents, chemical labels, a radiolabels, and fluorescent labels.

The carrier protein, in preferred examples, is ovalbumin. The carrier protein, in other preferred examples, is an IgG. In certain instances, it is advantageous to couple the C2 UDP-galactose analogue to biotin for detection. Subsequent detection of biotin can be carried out by chemiluminescent assay. The method as described herein is useful for imaging procedures, for example in magnetic resonance imaging.

Anticoagulation

Included in the invention are applications of the compositions of the invention as described herein are methods for preventing platelet aggregation. Platelet aggregation refers to the clumping together of platelets in the blood. Platelet aggregation is part of the sequence of events leading to the formation of a thrombus, or blood clot.

The invention describes methods for preventing platelet aggregation comprising administering to a subject an effective amount of a polypeptide fragment synthesized by the method comprising incubating a reaction mixture comprising a polypeptide fragment from a beta (1,4)-galactosyltransferase I with a sugar donor and an sugar acceptor and thereby preventing platelet aggregation. In the method, the polypeptide fragment may comprise an amino acid exchange at amino acid positions 285 and 340 corresponding to human beta (1,4)-galactosyltransferase I. The polypeptide fragment may comprise a conservative amino acid exchange at amino acid positions 289 and 344 corresponding to bovine beta (1,4)-galactosyltransferase I. A leucine (L) can be exchanged for a tyrosine (Y) at amino acid position 285 and a methionine (M) is exchanged for a histidine (H) at amino acid position 340. A leucine (L) can be exchanged for a tyrosine (Y) at amino acid position 289 and a methionine (M) is exchanged for a histidine (H) at amino acid position 344.

Included in the invention are methods for preventing platelet aggregation comprising administering to a subject an effective amount of a polypeptide fragment synthesized by the method comprising incubating a reaction mixture comprising a polypeptide fragment from a beta (1,4)-galactosyltransferase I, wherein the polypeptide fragment comprises SEQ ID NO: 2, with a sugar donor, wherein the sugar donor comprises a UDP-galactose analogue and a sugar acceptor in the presence of magnesium, thereby preventing platelet aggregation. In certain examples, the sugar donor is a UDP-galactose analogue. In the method, the sugar acceptor can be N-acetylglucosamine (GlcNAc). The N-acetylglucosamine (GlcNAc) can be free or attached to a peptide of a glycopeptide.

The method for preventing platelet aggregation can comprise administering to a subject an effective amount of an isolated glycoprotein synthesized by the method comprising incubating a reaction mixture comprising an isolated catalytic domain from a beta 1,4-galactosyltransferase I that catalyzes the formation of a GlcNAc-beta-1,4-N-acetylgalactosamine bond and a sugar donor, wherein the sugar donor comprises UDP-GalNAc or a UDP-GalNAc analogue. The isolated catalytic domain can comprise SEQ ID NO: 2.

The methods for preventing platelet aggregation as described herein are particularly useful for the treatment of diseases or disorders where platelet aggregation is abnormal or does not occur. For example, glanzmann thrombasthenia is a disease that is caused by a deficiency of a protein on the surface of the platelet, glycoprotein IIb/IIIa, and as a result, platelets do not aggregate or clot at the site of an injury. The Bernard-Soulier syndrome is caused by a lack or deficiency in the expression of the glycoprotein Ib/Ix complex on the surface of the platelets. This complex is the receptor for the von Willebrand factor (VWF). Due to lack or deficiency of expression the binding to the VWF does not occur at the site of vascular injury resulting in defective platelet adhesion.

Platelets can be affected by common drugs, including asprin, non-steroidal anti-inflammatory drugs like indomethacin, ibuprofen and naproxen, some heart drugs, some antibiotics, blood thinners, and antihistamines.

Therapeutic or Diagnostic Agents

A wide variety of agents may be included in the compounds of the present invention, such as any biologically active, therapeutic or diagnostic compound or composition. In general, the term bioactive agent includes, but is not limited to: polypeptides, including proteins and peptides (e.g., insulin); releasing factors and releasing factor inhibitors, including Luteinizing Hormone Releasing Hormone (LHRH) and gonadotropin releasing hormone (GnRH) inhibitors; carbohydrates (e.g., heparin); nucleic acids; vaccines; and pharmacologically active agents such as anti-infectives such as antibiotics and antiviral agents; anti-fungal agents; analgesics and analgesic combinations; anesthetics; anorexics; anti-helminthics; anti-arthritic agents; respiratory drugs, including anti-asthmatic agents and drugs for preventing reactive airway disease; anticonvulsants; antidepressants; anti-diabetic agents; anti-diarrheals; anticonvulsants; antihistamines; anti-inflammatory agents; toxins, anti-migraine preparations; anti-nauseants; anticancer agents, including anti-neoplastic drugs; anti-parkinsonism drugs; anti-pruritics; anti-psychotics; antipyretics; antispasmodics; anticholinergics; sympathomimetics; xanthine derivatives; cardiovascular preparations including potassium and calcium channel blockers, beta-blockers, alpha-blockers, cardioprotective agents; anti-arrhythmics; anti-hyperlipidemic agents; anti-hypertensives; diuretics; anti-diuretics; receptor agonists, antagonists, and/or mixed function agonist/antagonists; vasodilators including general coronary, peripheral and cerebral; central nervous system stimulants; vasoconstrictors; cough and cold preparations, including decongestants; enzyme inhibitors; hormones such as estradiol, testosterone, progesterone and other steroids and derivatives and analogs, including corticosteroids; hypnotics; hormonolytics; immunosuppressive agents; muscle relaxants; parasympatholytics; central nervous system stimulants; diuretics; hypnoticsleukotriene inhibitors; mitotic inhibitors; muscle relaxants; genetic material, including nucleic acid, RNA, DNA, recombinant RNA, recombinant DNA, antisense RNA, antisense DNA, hammerhead RNA, a ribozyme, a hammerheadribozyme, an antigene nucleic acid, a ribo-oligonucleotide, a deoxyribonucleotide, an antisense ribo-oligonucleotide, and/or an antisense deoxyribo-oligonucleotide; psychostimulants; sedatives; anabolic agents; vitamins; herbal remedies; anti-metabolic agents; anxiolytics; attention deficit disorder (ADD) and attention deficit hyperactivity disorder (ADHD) drugs; neuroleptics; and tranquilizers.

Application No. WO 2005/051429, incorporated by reference in its entirety herein, provides a list of exemplary agents that can be conjugated to the compositions of the instant invention.

Antibodies and Applications

As described herein, the targeting compound may be an antibody or a fragment thereof. The term "antibody" (Ab) or "monoclonal antibody" (Mab) is meant to include intact molecules as well as antibody portions (e.g., Fab and F (ab') 2 portions and Fv fragments) which are capable of specifically binding to a cell surface marker. Such portions are typically produced by proteolytic cleavage, using enzymes such as papain (to produce Fab portions) or pepsin (to produce F (ab')2 portions). Alternatively, antigen-binding portions can be produced through the application of recombinant DNA technology.

The immunoglobulin can be a "chimeric antibody" as that term is recognized in the art. Also, the immunoglobulin may be a bifunction or a hybrid antibody, that is, an antibody which may have one arm having a specificity for one antigenic site, such as a tumor associated antigen, while the other arm recognizes a different target, for example, a hapten which is, or to which is bound, an agent lethal to the antigen-bearing tumor cell. Alternatively, the bifunctional antibody may be one in which each arm has specificity for a different epitope of a tumor associated antigen of the cell to be therapeutically or biologically modified. In any case, the hybrid antibodies have a dual specificity, preferably with one or more binding sites specific for the hapten of choice or one or more binding sites specific for a target antigen, for example, an antigen associated with a tumor, an infectious organism, or other disease state.

Biological bifunctional antibodies are described, for example, in European Patent Publication, EPA 0 105 360, which is incorporated herein by reference. Hybrid or bifunctional antibodies may be derived biologically, by cell fusion techniques, or chemically, especially with cross-linking agents or disulfide bridge-forming reagents, and may be comprised of those antibodies and/or fragments thereof. Methods for obtaining such hybrid antibodies are disclosed, for example, in PCT application WO83/03679, published Oct. 27, 1983, and published European Application EPA 0 217 577, published Apr. 8, 1987, which are incorporated herein by reference. In one embodiment, the bifunctional antibodies are biologically prepared from a polydome or a quadroma, or are synthetically prepared with cross-linking agents such as bis-(maleimideo)-methyl ether ("BMME"), or with other cross-linking agents familiar to those skilled in the art.

In addition, the immunoglobin may be a single chain antibody ("SCA"). These may consist of single chain Fv fragments ("scFv") in which the variable light ("V [L]") and variable heavy ("V [H]") domains are linked by a peptide bridge or by disulfide bonds. Also, the immunoglobulin may consist of single V [H] domains (dAbs) which possess antigen-binding activity. See, e.g., G. Winter and C. Milstein, Nature, 349: 295 (1991); R. Glockshuber et al., Biochemistry, 29: 1362 (1990); and, E. S. Ward et al., Nature, 341: 544 (1989).

The antibodies may, in certain embodiments, be chimeric monoclonal antibodies. As used herein, the term "chimeric antibody" refers to a monoclonal antibody comprising a variable region, i.e., binding region, from one source or species and at least a portion of a constant region derived from a different source or species, usually prepared by recombinant DNA techniques.

Chimeric antibodies comprising a murine variable region and a human constant region are preferred in certain applications of the invention, particularly human therapy, because such antibodies are readily prepared and may be less immunogenic than purely murine monoclonal antibodies. Such murine/human chimeric antibodies are the product of expressed immunoglobulin genes comprising DNA segments encoding murine immunoglobulin variable regions and DNA segments encoding human immunoglobulin constant regions. Other forms of chimeric antibodies encompassed by the invention are those in which the class or subclass has been modified or changed from that of the original antibody. Such "chimeric" antibodies are also referred to as "class-switched antibodies." Methods for producing chimeric antibodies involve conventional recombinant DNA and gene transfection techniques well known in the art. See, e.g., Morrison, S. L. et al., Proc. Nat'l Acad. Sci., 81: 6851 (1984).

Encompassed by the term "chimeric antibody" is the concept of "humanized antibody," that is those antibodies in which the framework or "complementarity" determining regions ("CDR") have been modified to comprise the CDR of an immunoglobulin of different specificity as compared to that of the parent immunoglobulin. (See, e.g., EPA 0 239 400 (published Sep. 30, 1987)) In a preferred embodiment, a murine CDR is grafted into the framework region of a human antibody to prepare the "humanized antibody." See, e.g., L. Riechmann et al., Nature, 332: 323 (1988); M. S. Neuberger et al., Nature, 314: 268 (1985). Furthermore, the immunoglobulin (antibody), or fragment thereof, used in the present invention may be polyclonal or monoclonal in nature. Monoclonal antibodies are the preferred immunoglobulins. The preparation of such polyclonal or monoclonal antibodies is well known to those skilled in the art. See, e.g., G. Kohler and C. Milstein, Nature, 256: 495 (1975). The antibodies of the present invention may be prepared by any of a variety of methods. For example, cells expressing the cell surface marker or an antigenic portion thereof can be administered to an animal in order to induce the production of sera containing polyclonal antibodies. In a preferred method, a preparation of protein is prepared and purified so as to render it substantially free of natural contaminants. Such a preparation is then introduced into an animal in order to produce polyclonal antisera of greater specific activity. However, the present invention should not be construed as limited in scope by any particular method of production of an antibody whether bifunctional, chimeric, bifunctional-chimeric, humanized, or an antigen-recognizing fragment or derivative thereof.

In a preferred embodiment, the antibodies of the present invention are monoclonal antibodies (or portions thereof). Such monoclonal antibodies can be prepared using hybridoma technology (Kohler et al., Nature, 256: 495 (1975); Kohler et al., Eur. J. Immunol., 6: 511 (1976); Kohler et al, Eur. J. Immunol., 6: 292 (1976); Hammerling et al., In: "Monoclonal Antibodies and T-Cell Hybridomas," Elsevier, N.Y., pp. 563-681 (1981)). In general, such procedures involve immunizing an animal (preferably a mouse) with a protein antigen or with a protein-expressing cell (suitable cells can be recognized by their capacity to bind antibody). The splenocytes of such immunized mice are extracted and fused with a suitable myeloma cell line. Any suitable myeloma cell line may be employed in accordance with the present invention. After fusion, the resulting hybridoma cells are selectively maintained in HAT medium, and then cloned by limiting dilution as described by Wands et al., Gastroenterology, 80: 225-232 (1981). The hybridoma cells obtained through such a selection are then assayed to identify clones which secrete antibodies capable of binding the antigen. In addition, hybridomas and/or monoclonal antibodies which are produced by such hybridomas and which are useful in the practice of the present invention are publicly available from sources such as the American Type Culture Collection or commercial retailers.

The antibodies of the present invention may be labeled, for example, for detection or diagnostic purposes, e.g., imaging. Labels for the antibodies of the present invention include, but are not limited to, the following: examples of enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase; examples of radioisotopic labels include 3H, 111In, 125I, 131I, 32p, 35S, 14c, 51Cr, 57To, 58Co, 59Fe, 75Se, 152Eu, 90Y, 67Cu, 217Ci, 211At, 212Pb, 47Sc, and 109Pd; examples of suitable non-radioactive isotopic labels include 157Gd, 55Mn, 52Tr, and 56Fe; examples of fluorescent labels include an 152 Eu label, a fluorescein label, an isothiocyanate label, a rhodamine label, a phycoerythrin label, aphycocyanin label, an allophycocyanin label, an o-phthaldehyde label, and a fluorescamine label; examples of toxin labels include diphtheria toxin, ricin, and cholera toxin; examples of chemiluminescent labels include a luminal label, an isoluminal label, an aromatic acridinium ester label, an imidazole label, an acridinium salt label, an oxalate ester label, a luciferin label, a luciferase label, and an aequorin label; and examples of nuclear magnetic resonance contrasting agents include heavy metal nuclei such as Gd, Mn, and Fe. Typical techniques for binding the above-described labels to antibodies are provided by Kennedy et al., Clin. Chim. Acta, 70:1-31 (1976), and Schurs et al., Clin. Chim. Acta, 81: 1-40 (1977), which are incorporated by reference In one embodiment, the glycoconjugates of the invention include monoclonal antibodies, such as those directed against tumor antigens, for use as cancer therapeutics. Generally, monoclonal antibodies have one N-linked bi-antennary oligosaccharide attached at the IgG-Fc region. The terminal sugars of the oligosaccharide moiety come in several glycoforms, for example, some are desialated, degalactosylated, with only terminal N-acetylglucosaminyl residues.

The monoclonal antibodies carrying only terminal N-acetylgucosamine on the bi-antennary oligosaccharide moieties, the Goglycoform, can be generated by de-sialylation and de-galactosylation of the monoclonal antibodies. With the mutant Tyr289Leu-Gal-T1 (Y289LGalT1) and UDP-a-galactose-C-2-modified, a galactose moiety that has a chemically reactive group attached at the C2 position of galactose, can then be transferred to Go glycoform of the monoclonal antibody. The chemically reactive group can include, for example, a ketone moiety that can serve as a neutral, yet versatile chemical handle to add other agents, such as bioactive agents, to the compound.

Methods of Treatment

The instant invention provides enzymes and methods that can be used to promote the chemical linkage of biological molecules, and thus provides a means to link agents for therapeutic application. Moreover, the instant invention provides a means to carry out the method in a physiological setting.

Accordingly, the invention features methods for the diagnosis or treatment of a subject suffering from a disease or disorder. The methods comprise administering to the subject an effective amount of polypeptide fragment synthesized by the method comprising incubating a reaction mixture comprising an isolated catalytic domain from a beta (1,4)-galactosyltransferase I with a sugar donor, wherein one or more agents are linked to the sugar donor, and an sugar acceptor thereby diagnosing or treating the subject.

The polypeptide fragment may comprise an amino acid exchange at amino acid positions 285 and 340 corresponding to human beta (1,4)-galactosyltransferase I. Further, a leucine (L) may be exchanged for a tyrosine (Y) at amino acid position 285 and a methionine (M) is exchanged for a histidine (H) at amino acid position 340, in certain preferred embodiments.

The polypeptide fragment may comprise a conservative amino acid exchange at amino acid positions 289 and 344 corresponding to bovine beta (1,4)-galactosyltransferase I. Further, a leucine (L) is exchanged for a tyrosine (Y) at amino acid position 289 and a methionine (M) is exchanged for a histidine (H) at amino acid position 344 in certain preferred embodiments.

In certain preferred embodiments, the polypeptide fragment comprises SEQ ID NO: 2.

Disease states needing treatment are only limited by current available therapeutics. As described herein, the methods of the invention are useful for engineering of nanoparticles, including multivalent nanoparticles, carrying any number of therapeutic agents. For example, the nanoparticles can be used to treat cancer, inflammatory disease, cardiovascular disease, obesity, ageing, bacterial infection, or any other disease amenable to therapy.

The glycoconjugates compositions of the invention can be used to treat and/or diagnose a variety of diseases and/or disorders. For example, the glycoconjugates compositions of the invention are used for specific, targeted delivery of bioactive agents, including toxic drugs, agents for imaging or diagnostics, (e.g., toxins, radionuclides), to therapeutically-relevant tissues or cells of the body, for example, tumors. In another embodiment of the invention, the glycoconjugates compositions of the invention are used to deliver bioactive agents, including DNA vectors, to cells.

As further examples, the glycoconjugates compositions of the invention are useful for the treatment of a number of diseases and/or disorders including, but not limited to: cancer, both solid tumors as well as blood-borne cancers, such as leukemia; hyperproliferative disorders that can be treated by the compounds of the invention include, but are not limited to, neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

The glycoconjugates of the invention can be used to treat cardiovascular diseases and disorders including, but not limited to, myocardial infarction (heart attack), cerebrovascular diseases (stroke), transient ischaemic attacks (TIA), peripheral vascular diseases, arteriosclerosis, angina, high blood pressure, high cholesterol, arrhythmia.

The glycoconjugates of the invention can be used to treat genetic diseases, such as enzyme deficiency diseases.

The glycoconjugates of the invention can be used to treat hyperproliferative disorders. Examples of such hyperproliferative disorders that can be treated by the glycoconjugates of the invention are as described in Application WO 2005/051429, and are incorporated by reference in its entirety herein.

The glycoconjugates of the present invention are also useful for raising an immune response against infectious agents. Viruses are one example of an infectious agent that can cause disease or symptoms that can be treated by the compounds of the invention. Examples of viruses that can cause disease or symptoms and that can be treated by the glycoconjugates of the invention are as described in Application WO 2005/051429, and are incorporated by reference in its entirety herein.

Similarly, bacterial or fungal agents that can cause disease or symptoms and that can be treated by the glycoconjugates of the invention are as described in Application WO 2005/051429, and are incorporated by reference in its entirety herein.

Additionally, the glycoconjugates of the invention are useful for treating autoimmune diseases. An autoimmune disease is characterized by the attack by the immune system on the tissues of the victim. Autoimmune disease is characterized by the inability of the recognition of "self" and the tissue of the afflicted subject is treated as a foreign target. The compounds of the present invention are therefore useful for treating autoimmune diseases by desensitizing the immune system to these self antigens by provided a TCR signal to T cells without a costimulatory signal or with an inhibitory signal. Examples of autoimmune diseases which may be treated using the glycoconjugates of the present invention are as described in Application WO 2005/051429, and are incorporated by reference in its entirety herein.

Similarly, allergic reactions and conditions, such as asthma (particularly allergic asthma) or other respiratory problems, may also be treated by glycoconjugates of the invention. Moreover, the glycoconjugates of the invention can be used to treat anaphylaxis, hypersensitivity to an antigenic molecule, or blood group incompatibility.

The glycoconjugates of the invention which can inhibit an immune response are also useful for treating and/or preventing organ rejection or graft versus host disease, atherosclerosis; olitis; regional enteritis; adult respiratory distress syndrome; local manifestations of drug reactions, such as dermatitis, etc.; inflammation-associated or allergic reaction patterns of the skin; atopic dermatitis and infantile eczema; contact dermatitis; psoriasis; lichen planus; allergic enteropathies; allergic rhinitis; bronchial asthma; hypersensitivity or destructive responses to infectious agents; poststreptococcal diseases, e.g., cardiac manifestations of rheumatic fever, and the like.

Vaccines

The invention also provides methods for eliciting an immune response in a mammal such as a human, including administering to a subject an immunological composition comprising a compound or composition as described herein. Therefore, one embodiment of the present invention is to use the glycoconjugates described herein in an immunological preparation.

The immunological composition according to the instant invention may be prepared by any method known in the art. For example, glycoconjugates of the present invention are prepared and are then injected into an appropriate animal. The compositions according to the present invention may be administered in a single dose or they may be administered in multiple doses, spaced over a suitable time scale to fully utilize the secondary immunization response. For example, antibody titers may be maintained by administering boosters once a month. The vaccine may further comprise a pharmaceutically acceptable adjuvant, including, but not limited to Freund's complete adjuvant, Freund's incomplete adjuvant, lipopolysaccharide, monophosphoryl lipid A, muramyl dipeptide, liposomes containing lipid A, alum, muramyl tripeptide-phosphatidylethanoloamine, keyhole and limpet hemocyanin.

Administration

The compositions of the present invention may be administered by any means that results in the contact of the bioactive agent with the agent's site or site(s) of action on or in a subject, e.g., a patient. The compositions may be administered alone or in conjunction with one or more other therapies or treatments.

The targeted glycoconjugates produced according to the present invention, can be administered to a mammalian host by any route. Thus, as appropriate, administration can be orally, intravenously, rectally, parenterally, intracistemally, intradermally, intravaginally, intraperitoneally, topically (as by powders, ointments, gels, creams, drops or transdermal patch), bucally, or as an oral or nasal spray. The term "parenteral" as used herein refers to modes of administration which include intravenous, intramuscular, intraperitoneal, intrasternal, subcutaneous and intraarticular injection and infusion. Parenteral administration in this respect includes administration by the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol and rectal systemic.

In addition, administration can be by periodic injections of a bolus of the therapeutic or can be made more continuous by intravenous or intraperitoneal administration from an external source. In certain embodiments, the therapeutics of the instant invention can be pharmaceutical-grade and incompliance with the standards of purity and quality control required for administration to humans. Veterinary applications are also within the intended meaning as used herein.

The formulations, both for veterinary and for human medical use, of the therapeutics according to the present invention typically include such therapeutics in association with a pharmaceutically acceptable carrier therefor and optionally other ingredient (s). The carrier (s) can be acceptable in the sense of being compatible with the other ingredients of the formulations and not deleterious to the recipient thereof. Pharmaceutically acceptable carriers are intended to include any and all solvents, dispersion media, coatings, antibacterial and antifungal agents, isotonic and absorption delaying agents, and the like, compatible with pharmaceutical administration.

A pharmaceutical composition of the invention is formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such asethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Useful solutions for oral or parenteral administration can be prepared by any of the methods well known in the pharmaceutical art, described, for example, in Remington's Pharmaceutical Sciences. Formulations for parenteral administration also can include glycocholate for buccal administration, methoxysalicylate for rectal administration, or citric acid for vaginal administration. The parenteral preparation can be enclosed in ampoules, disposable syringes or multiple dose vials made of glass or plastic.

Formulations of the present invention suitable for oral administration can be in the form of discrete units such as capsules, gelatin capsules, sachets, tablets, troches, or lozenges, each containing a predetermined amount of the drug; in the form of a powder or granules; in the form of a solution or a suspension in an aqueous liquid or non-aqueous liquid; or in the form of an oil-in-water emulsion or a water-in-oil emulsion. The therapeutic can also be administered in the form of a bolus, electuary or paste. A tablet can be made by compressing or molding the drug optionally with one or more accessory ingredients. Compressed tablets can be prepared by compressing, in a suitable machine, the drug in a free-flowing form such as a powder or granules, optionally mixed by a binder, lubricant, inert diluent, surface active or dispersing agent. Molded tablets can be made by molding, in a suitable machine, a mixture of the powdered drug and suitable carrier moistened with an inert liquid diluent.

Oral compositions generally include an inert diluent or an edible carrier.

For the purpose of oral therapeutic administration, the active compound can be incorporated with excipients. Oral compositions prepared using a fluid carrier for use as a mouthwash include the compound in the fluid carrier and are applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gumtragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the composition can be sterile and can be fluid to the extent that easy syringability exists. It can be stable under the conditions of manufacture and storage and can be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by sterilization, e.g., filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient.

Formulations suitable for topical administration, including eye treatment, include liquid or semi-liquid preparations such as liniments, lotions, gels, applicants, oil-in-water or water-in-oil emulsions such as creams, ointments or pasts; or solutions or suspensions such as drops. Formulations for topical administration to the skin surface can be prepared by dispersing the therapeutic with a dermatologically acceptable carrier such as a lotion, cream, ointment or soap. In some embodiments, useful are carriers capable of forming a film or layer over the skin to localize application and inhibit removal.

For inhalation treatments, such as for asthma, inhalation of powder (self-propelling or spray formulations) dispensed with a spray can, a nebulizer, or an atomizer can be used. Such formulations can be in the form of a finely comminuted powder for pulmonary administration from a powder inhalation device or self-propelling powder-dispensing formulations. In the case of self-propelling solution and spray formulations, the effect can be achieved either by choice of a valve having the desired spray characteristics (i.e., being capable of producing a spray having the desired particle size) or by incorporating the active ingredient as a suspended powder in controlled particle size. For administration by inhalation, the therapeutics also can be delivered in the form of an aerosol spray from a pressured container or dispenser which contains a suitable propellant, e.g., a gas such as carbon dioxide, or a nebulizer. Nasal drops also can be used.

Systemic administration also can be by transmucosal or transdermal means. For transmucosal or transdermal administration, penetrants appropriate to the barrier to be permeated are used in the formulation. Such penetrants generally are known in the art, and include, for example, for transmucosal administration, detergents, bile salts, and filsidic acid derivatives. Transmucosal administration can be accomplished through the use of nasal sprays or suppositories. For transdermal administration, the therapeutics typically are formulated into ointments, salves, gels, or creams as generally known in the art.

The therapeutics can be prepared with carriers that will protect against rapid elimination from the body, such as a controlled release formulation, including implants and microencapsulated delivery systems.

The compounds of the invention may also suitably be administered by sustained-release systems. Suitable examples of sustained-release compositions include semipermeable polymer matrices in the form of shaped articles, e.g., films, or mirocapsules. Sustained-release matrices include polylactides (U.S. Pat. No. 3,773,919, EP 58, 481), copolymers of L-glutamic acid and gamma-ethyl-L-glutamate (U. Sidman et al., Biopolymers 22: 547-556 (1983)), poly (2-hydroxyethyl methacrylate) (R. Langer et al., J. Biomed. Mater. Res. 15: 167-277 (1981), and R. Langer, Chem. Tech. 12: 98-105 (1982)), ethylene vinyl acetate (R. Langer et al., Id.) or poly-D-(−)-3-hydroxybutyric acid (EP 133,988). Sustained-release compositions also include liposomally entrapped compositions of the present invention (Epstein, et al., Proc. Natl. Acad. Sci. USA 82: 3688-3692 (1985); Hwang et al., Proc. Natl. Acad. Sci. USA 77: 4030-4034 (1980).

The compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Generally, the therapeutics identified according to the invention can be formulated for administration to humans or other mammals, for example, in therapeutically effective amounts, e.g., amounts which provide appropriate concentrations of the bioactive agent to target tissue/cells for a time sufficient to induce the desired effect. Additionally, the therapeutics of the present invention can be administered alone or in combination with other molecules known to have a beneficial effect on the particular disease or indication of interest. By way of example only, useful cofactors include symptomalleviating cofactors, including antiseptics, antibiotics, antiviral and antifungal agents and analgesics and anesthetics.

The effective concentration of the therapeutics identified according to the invention that is to be delivered in a therapeutic composition will vary depending upon a number of factors, including the final desired dosage of the drug to be administered and the route of administration. The preferred dosage to be administered also is likely to depend on such variables as the type and degree of the response to be achieved; the specific composition of another agent, if any, employed; the age, body weight, general health, sex and diet of the patient; the time of administration, route of administration, and rate of excretion of the composition; the duration of the treatment; bioactive agent (such as a chemotherapeutic agent) used in combination or coincidental with the specific composition; and like factors well known in the medical arts. In some embodiments, the therapeutics of this invention can be provided to an individual using typical dose units deduced from the earlier-described mammalian studies using non-human primates and rodents. As described above, a dosage unit refers to a unitary, i.e. a single dose which is capable of being administered to a patient, and which can be readily handled and packed, remaining as a physically and biologically stable unit dose comprising either the therapeutic as such or a mixture of it with solid or liquid pharmaceutical diluents or carriers.

Therapeutics of the invention also include "prodrug" derivatives. The term prodrug refers to a pharmacologically inactive (or partially inactive) derivative of a parent molecule that requires biotransformation, either spontaneous or enzymatic, within the organism to release or activate the active component. Prodrugs are variations or derivatives of the therapeutics of the invention which have groups cleavable under metabolic conditions. Prodrugs become the therapeutics of the invention which are pharmaceutically active in vivo, when they undergo solvolysis under physiological conditions or undergo enzymatic degradation. Prodrug forms often offer advantages of solubility, tissue compatibility, or delayed release in the mammalian organism (see, Bundgard, Design of Prodrugs, pp. 7-9, 21-24, Elsevier, Amsterdam 1985 and Silverman, The Organic Chemistry of Drug Design and Drug Action, pp. 352-401, Academic Press, San Diego, Calif., 1992).

Kits

Also included in the invention are kits. Preferably, kits comprise a packaging material, and a polypeptide fragment from a beta (1,4)-galactosyltransferase I according to any one of the aspects of the invention as described herein. The kits, in certain preferred embodiments, comprise a sugar donor. The donor can be any one of UDP-galactose, UDP-GalNAc, UDP-GalNAc analogues or UDP-Galactose analogues. The kits can also comprise an agent. In preferred examples, the agent is linked to the sugar donor. Exemplary agents are described in this disclosure. Certain agents can be selected from antibodies, single chain antibodies, bacterial toxins, growth factors, therapeutic agents, contrast agents, targeting agents, chemical labels, a radiolabels, and fluorescent labels.

EXAMPLES

It should be appreciated that the invention should not be construed to be limited to the examples that are now described; rather, the invention should be construed to include any and all applications provided herein and all equivalent variations within the skill of the ordinary artisan.

As described in more detail below, the experiments reported herein are based on the finding that the genetically engineered beta Gal-TI enzyme, Gal-T1-Y289L-M344H, which can transfer GalNAc or 2' modified galactose to GlcNAc residue of a glycan chain in the presence of magnesium instead of manganese, is very useful for the synthesis of a disaccharide unit with a chemical handle on the glycan chain of glycoconjugates on live cells. Since, in contrast to manganese, the concentration of magnesium used is not toxic to cells, the galactose with a chemical handle transferred by the mutant enzyme can be used for detection of available GlcNAc residues on a given live cell under different physiological states or for conjugation of pharmacological agents for therapeutic purposes.

Example 1

The GalT1-Y289L-M344H Double Mutant Transfers Sugar in the Presence of Mg2+

X-ray crystal structures of the catalytic domain of many glycosyltransferases have been determined in recent years, and these studies show that the specificity of the sugar donor is determined by residues in the sugar-nucleotide binding pocket of glycosyltransferases. This structural information has made it possible to reengineer the existing glycosyltransferases. For example, the beta 1,4-galactosyltranferase family in vertebrates (beta 4Gal-T1 to T7) is responsible for the transfer of galactose from the donor UDP-galactose (UDP-Gal) to various glycans in a beta 1-4 linkage (Amado et al, 1999; Hennet et al., 2002)). The residue Tyr289 (or Phe) in the catalytic pocket of b4Gal-T1, determines the sugar donor substrate specificity of the enzyme toward UDP-Gal (Qasba et al., 2005; Ramakrishnan et al. 2002). Mutation of Tyr289 to Leu or Ile enlarges the binding pocket such that the mutant enzyme, beta4Gal-T1-Y289L, has beta 1,4-Nacetylgalactosaminyltransferase (beta 4GalNAc-T) activity, which is as efficient as its beta-1,4-galactosyltransferase (beta 4Gal-T) activity (Ramakrishnan et al. 2002; Ramakrishnan et al. 2004). Similarly, in blood group A GalNAc-transferase, the residues Leu266 and Gly268, and in blood group B Gal transferase, the residues Met266 and Ala268 determine the specificities toward their respective sugar donors, UDP-GalNAc and UDP-Gal (Marcus et al. 2003). Mutation of Met266 to Leu266 in blood group B Gal-transferase changes the enzyme sugar donor specificity toward UDP-GalNAc. Furthermore, in beta 1,3-glucuronyltransferase-1 (GlcA-T1), His 308 (His 311 in GlcAT-P) (Pederson et al, 2002; Kakuda et al., 2004) determines the enzyme specificity toward the sugar donor UDP-GlcUA. Mutation of His308 to Arg308 changes the specificity of the sugar donor to UDP-Glc, UDP-Man, or UDP-GlcNAc.

It has previously been shown that the sugar donor specificity of beta 4Gal-T1 toward UDP-Gal is determined by a single amino acid, Tyr, at position 289 (Ramakrishnan, B., et al. 2002). When Tyr289 is mutated to Leu, the sugar donor specificity of â4Gal-T1 is broadened in a way that, in contrast to the wild-type enzyme which lacks GalNAc-T activity, the mutant beta 4Gal-T1-Y289L exhibits both beta 4Gal-T and beta 4GalNAc-T activities. The Tyr289 mutant can also transfer from the UDP derivatives the galactose moiety that has, at the C2 position, substitutions other than the 2-N-acetyl group (—NH—CO—CH3 in GalNAc) (21). Described herein is the transfer of GalNAc to N-glycans of glycoproteins by a GalT1-Y289L-M344H double mutant.

The instant invention describes a novel GalT1-Y289L-M344H double mutant that is still functional, that is the GalT1-Y289L-M344H double mutant is able to transfer sugar in the presence of magnesium.

Beta-1,4-galactosyltransferase (beta4Gal-T1) in the presence of manganese ion (Mn2+) transfers galactose from UDP-galactose (UDP-Gal) to N-acetylglucosamine (GlcNAc) that is either free or linked to an oligosaccharide. Crystallographic studies on bovine beta4Gal-T1 have shown that the primary metal binding site is located in the hinge region of a long flexible loop, which upon Mn (2+) and UDP-Gal binding changes from an open to a closed conformation. This conformational change creates an oligosaccharide binding site in the enzyme.

The results presented here demonstrate transfer of GalNAc or a modified sugar by the double mutant, beta 4Gal-T1-M340H_Y285L, in the presence of Mg2+. This is in contrast to the single mutant b4Gal-T1Y289L or the wild type b4Gal-T1, which both require the presence of Mn2+ for the transfer of GalNAc or a modified sugar. The experiments shown in FIG. 1 were performed with the double mutant, b4Gal-T1_M340H_Y285L, which was constructed from the single mutants, b4Gal-T1_M340H and b4Gal-T1_Y285L. The b4Gal-T1-M340H single mutant requires Mg2+ for the transfer reaction, while the b4Gal-T1 Y285L single mutant requires Mn2+ for the transfer reaction. In FIGS. 1, (A), (B) and (C) show the MALDI mass spectra of glycans after the transfer of GalNAc (shown in B) or 2-keto-galactose (shown in C) to the sugar acceptor, heptasaccharide tetrapeptide (A), Arg-[GlcNAcβ1,2-Manα-1,6-(GlcNAcβ1,2-Manα1,3)-Manβ1,4-GlcNAcβ1,4-GlcNAcβ]-Asn-Glu-Gly, by the double mutant enzyme, b4Gal-T1M340H_Y285L. In FIG. 1, major peaks are annotated with the carbohydrate structure shown in the symbols for monosaccharides, according to the nomenclature adopted by the consortium for functional glycomics (publicly available on the world wide web at functional glycomics.org/static/consortium/). Panel (A) shows a peak at 1773.9 m/z corresponding to the starting branched heptasaccharide tetrapeptide. Panel (B) shows a peak at 2179.0 m/z corresponding to a nanosaccharide tetrapeptide having two added GalNAc moieties as indicated and Panel (C) the peak at 2178 m/z corresponding to a nanoasaccharide tetrapeptide having two added 2-keto-galactose moieties as indicated.

Figure 2:
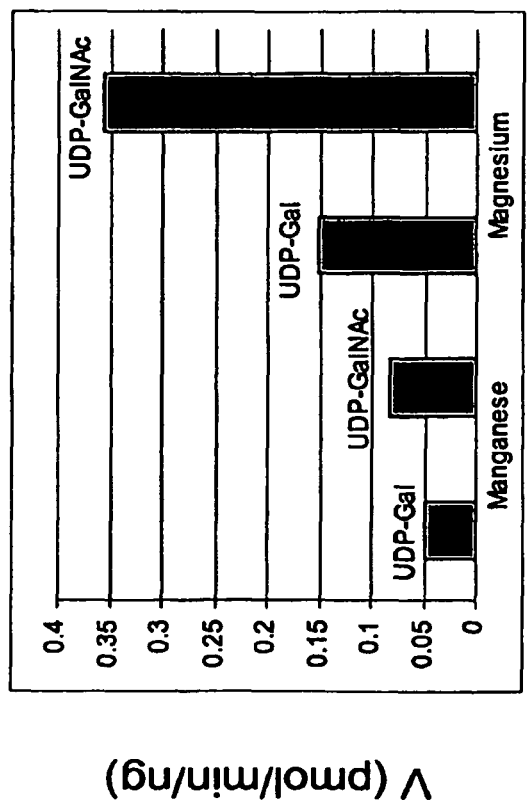
FIG. 2 is a graph showing specific activities of the catalytic domain of the human beta 4Gal-T1-M340H-Y285L. Reactions were performed under saturating conditions of all substrates. In these reactions the concentrations for the donors UDP-galactose or UDP-GalNAc was 500 μM and the acceptor β-benzyl-GlcNAc was at 25 mM.

FIG. 2 shows the specific activities of the catalytic domain of the human b4Gal-T1-M340H-Y285L in the presence of manganese or magnesium. The reactions were performed under saturating conditions of all substrates. The results presented in FIG. 2 show that the catalytic domain of the human b4Gal-T1-M340H-Y285L is active in the presence of magnesium. This is in contrast to the wild type, which is not active (not able to transfer sugar) in the presence of magnesium.

Example 2

GalT1-Y289L-M344H Prevents Platelet Aggregation

The double mutant enzyme GalT1-Y289L-M344H has use as an anticoagulation agent. It was found that the double mutant enzyme can transfer galactose using 50-75 micromolar concentrations of UDP-galactose in the presence of magnesium to platelets and thus prevent their aggregation in the cold. In contrast, the wild type enzyme requires 800 micromolar concentrations of UDP-galactose at high concentrations of Ca2+ with a low concentration of manganese (data not shown).

Methods

The Invention was Performed Using the Following Methods:
Met344His Mutant

Site-directed mutagenesis was performed using the PCR method. Construction of the mutants was carried out as described previously in Qasba et al. (Biochemistry 2004, 43, 12513-12522), incorporated by reference in its entirety herein.

Bacterial Growth and Plasmid Transformation

Bacterial growth and plasmid transformations can be performed using standard procedures (Ausubel et al., Current Protocols in Molecular Biology, Greene Publishing Associates and Wiley-Interscience, New York (1987)). US Published Application 20060084162, incorporated by reference in its entirety herein, describes methods for bacterial growth and transformation using the plasmid pEGT-d129, which encodes the catalytic domain (residues 130-402) of bovine .beta.(1,4)-galactosyltransferase I. Site-directed mutagenesis can be performed using a CLONTECH site-directed mutagenesis transformer kit. Thus, the transformation mixture contains the template pEGT-d129, a selection primer, and a mutagenic primer for creation of a desired mutant. Mutants are screened for the incorporated mutations by looking for changes in restriction enzyme digestion patterns and confirmed by DNA sequencing. The positive clones were transformed into B834(DE3)pLysS cells.

Expression and Purification of Inclusion Bodies

The expression and purification of the inclusion bodies can be carried out as described previously (Ausubel et al., Current Protocols in Molecular Biology, Greene Publishing Associates and Wiley-Interscience, New York (1987)). The inclusion bodies are S-sulfonated by dissolving in 5 M GdnHCl, 0.3 M sodium sulfite, and the addition of di-sodium 2-nitro-5-thiosulfobenzoate to a final concentration of 5 mM. The sulfonated protein is precipitated by dilution with water, and the precipitate was washed thoroughly.

Briefly, 100 mg of sulfonated protein is folded in one liter folding solution for 48 hours. Inclusion of 10% glycerol and 10 mM lactose in the folding solution enhances the folding efficiency of the galactosyltransferase, e.g. beta-1,4-galactosyltransferase (beta4Gal-T1). After refolding the protein, the folding solution is extensively dialyzed against water. During dialysis the misfolded protein precipitates out, while the folded protein remains soluble. The soluble protein is first concentrated and then purified on a Ni-column. Nearly 2 mg of folded ppGalNAc-T2 protein is obtained form 1 liter of folding solution. Purified protein may be tested for catalytic activity using a 13 amino acid peptide, PTTDSTTPAPTTK, as an acceptor using methods described previously (Fritz. T. A et al. J Biol Chem. 2006).

Improving the folding conditions: In recent years factorial folding screens (Rudolph and Lilie, FASEB J., 10:40-56 (1996); Chen and Gouaux, Proc. Natl. Acad. Sci., 94:13431-13436 (1997); Armstrong et al., Prot. Sci., 8:1475-1483 (1999)) have been developed for examining the folding efficiencies of proteins from inclusion bodies. To improve the in vitro folding efficiency, 8 different folding conditions similar to the formulations described in the FoldIt Screen kit (Hampton Research, Calif.) with certain modifications were tested. Condition I: 50 mM Tris-HCl pH 8.0, 5 mM EDTA, 0.5 M guanidine-HCl, 8 mM cysteamine and 4 mM cystamine. Condition II: 55 Mes pH 6.5, 10.56 mM NaCl, 0.44 mM KCl, 2.2 mM MgCl.sub.2, 2.2 mM CaCl.sub.2, 0.5 M guanidine-HCl. Condition III: similar to condition II with respect to the buffer, pH, chaotrope and salt condition, but it had 0.055% PEG-4000, 1.1 mM EDTA, 0.44 M sucrose and 0.55 M L-arginine. Condition IV: 55 mM Mes pH 6.5, 264 mM NaCl, 11 mM KCl, 0.055% PEG-4000, 0.5 M guanidine-HCl, 2.2 mM MgCl2, 2.2 mM CaCl.sub.2 and 0.44 M sucrose. Condition V: 55 mM Tris pH 8.2, 10.56 mM NaCl, 0.44 mM KCl, 1.1 mM EDTA, 0.44 M sucrose. Conditions VI and VIII are similar except for the presence of redox agents. Condition VII: 55 mM Mes pH 6.5, 264 mM NaCl, 11 mM KCl, 1.1 mM EDTA, 0.5 M guanidine-HCl, and 0.55 M L-arginine. The buffers II through VII had 100 mM GSH and 10 mM GSSG. Conditions I and VIII, had 8 mM cysteamine and 4 mM cystamine. Condition VIII, gave the highest enzymatic activity, soluble and folded protein, was 50 mM Tris-HCl pH 8.0, 10.56 mM NaCl, 0.44 mM KCl, 2.2 mM MgCl2, 2.2 mM CaCl.sub.2 0.5 M guanidine-HCl, 8 mM cysteamine and 4 mM cystamine, 0.055% PEG-4000 and 0.55 M L-arginine.

Mutation

Mutation of certain amino acid residues as described herein is, in certain examples, performed site-directed mutagenesis. US Published Application 20060084162 describes methods for site directed mutagensis of amino acid position 289 of the bovine .beta.(1,4)-galactosyltransferase I, performed using the PCR method.

Gal-T and GalNAc-T Enzyme Assays

Gal-T and GalNAc T enzyme assays are easily performed according to methods described in the art, for example US Published Application 20060084162. Protein concentrations are measured using the Bio-Rad protein assay kit, based on the method of Bradford and further verified on SDS gel. An in vitro assay procedure for the Gal-T1 has been reported previously (Ramakrishnan et al., J. Biol. Chem., 270, 87665-376717 (2001)). The activities were measured using UDP-Gal or UDP-GalNAc as sugar nucleotide donors, and GlcNAc and Glc as the acceptor sugars. For the specific activity measurements, a 100-.mu.l incubation mixture containing 50 mM .beta.-benzyl-GlcNAc, 10 mM MnCl.sub.2, 10 mM Tris-HCl, pH 8.0, 500 .mu.M UDP-Gal or UDP-GalNAc, 20 ng of Gal-T1, and 0.5 .mu.Cl of [.sup.3H]UDP-Gal or [.sup.3H]UDP-GalNAc was used for each Gal-T or Gal-NAc-T reaction. The incubation was carried out at 37.degree. C. for 10 min. The reaction was terminated by adding 200 .mu.l of cold 50 mM EDTA, and the mixture was passed through a 0.5-ml bed volume column of AG1-X8 cation resin (Bio-Rad) to remove any unreacted [.sup.3H]UDP-Gal or [.sup.3H]UDP-GalNAc. The column was washed successfully with 300, 400, and 500 .mu.l of water, and the column flow-through was diluted with Biosafe scintillation fluid; radioactivity was measured with a Beckman counter. A reaction without the acceptor sugar was used as a control. A similar assay was carried out to measure the GalNAc-T activity with Glc and other acceptors in the presence of 50 .mu.M bovine LA (Sigma).

The in vitro assay for enzyme activity (beta Gal T1, double mutant beta-gal) can be performed as described (Boeggeman et al., Glycobiology, 12:395-407 (2002)). The .sup.3H-labeled-UDP-Gal or UDP-Galactose was used as sugar donor and GlcNAc as the sugar acceptor. A reaction without GlcNAc was used as a control.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

REFERENCES

Amado, M., Almeida, R., Schwientek, T., and Clausen, H. (1999) Identification and characterization of large galactosyltransferase gene families: galactosyltransferases for all functions. Biochim. Biophys. Acta 1473, 35-53.

Bell, J. E., Beyer, T. A., and Hill, R. (1976) The kinetic mechanism of bovine milk galactosyltransferase. The role of R-lactalbumin, J. Biol. Chem. 251, 3003-3013.

Berger, E. G. and Rohrer, J. (2003) Galactosyltransferase—still up and running. Biochimie 85, 261-274.

Boeggeman, E., and Qasba, P. K. (2002) Studies on the metal binding sites in the catalytic domain of â1,4-galactosyltransferase, Glycobiology 12, 395-407.

Boeggeman, E., Balaji, P. V., Sethi, N., Masibay, A. S., and Qasba, P. K. (1993) Expression of deletion constructs of bovine beta-1,4-galactosyltransferase in *Escherichia coli*: importance of Cys134 for its activity, Protein Eng. 6, 779-785.

Boeggeman, E. E., Ramakrishnan, B. and Qasba, P. K. The N-terminal stem region of bovine and human beta1,4-galactosyltransferase I increases the in vitro folding efficiency of their catalytic domain from inclusion bodies. Protein Expr Purif. (2003) 30, 219-29.

Boeggeman E. E., Ramakrishnan B., Kilgore C., Khidekel N., Hsieh-Wilson L. C., Simpson J. T., and Qasba P. K. Direct Identification of Nonreducing GlcNAc Residues on N-Glycans of Glycoproteins Using a Novel Chemoenzymatic Method. Bioconjugate Chem. 2007, 18, 806-814.

Boix, E. et al. (2001) Structure of UDP complex of UDP-galactose: b-galactoside-a-1,3-galactosyltransferase at 1.53-A° resolution reveals a conformational change in the catalytically important C terminus. J. Biol. Chem. 276, 48608-48614

Brew, K., Vanaman, T. C., and Hill, R. L. (1968) The role of R-lactalbumin and the A protein in lactose synthetase: a unique mechanism for the control of a biological reaction, Proc. Natl. Acad. Sci. U.S.A. 59, 491-497.

Brodbeck, U., Denton, W. L., Tanahashi, N., and Ebner, K. E. (1967) The isolation and identification of the B protein of lactose synthetase as R-lactalbumin, J. Biol. Chem. 242, 1391-1397.

Fritz. T. A., Raman, J., and Tabak, L. A. Dynamic association between the catalytic and lectin domains of human UDP-GalNAc:polypeptide alpha-N-acetylgalactosaminyltransferase-2. J Biol Chem. (2006) 281, 8613-9.

Gastinel, L. N., Cambillau, C., and Bourne, Y. (1999) Crystal structures of the bovine â4-galactosyltransferase catalytic domain and its complex with uridine diphosphogalactose, EMBO J. 18, 3546-3557.

Geren, C. R., Magee, S. C., and Ebner, K. E. (1975) Circular dichroism changes in galactosyltransferase upon substrate binding, Biochemistry 14, 1461-1463.

Gunasekaran, K., Buyong, M., Ramakrishnan, B., Qasba, P. K., and Nussinov, R. (2003) Interdependence of backbone flexibility, residue conservation, and enzyme function: a case study on beta1,4-galactosyltransferase-I, Biochemistry 42, 3674-3687.

Hennet, T. (2002) The galactosyltransferase family. Cell. Mol. Life Sci. 59, 1081-1095.

Hu, Y. et al. (2003) Crystal structure of the MurG:UDP-GlcNAc complex reveals common structural principles of a superfamily of glycosyltransferases. Proc. Natl. Acad. Sci. U.S.A. 100, 845-849

Kakuda, S., Shiba, T., Ishiguro, M., Tagawa, H., Oka, S., Kajihara, Y., Kawasaki, T., Wakatsuki, S., and Kato, R. (2004) Structural basis for acceptor substrate recognition of a human glucuronyltransferase, GlcAT-P, an enzyme critical in the biosynthesis of the carbohydrate epitope HNK-1. J. Biol. Chem. 279, 22693-22703.

Lobsanov, Y. D. et al. (2004) Structure of Kre2p/Mnt1p: a yeast a1,2-mannosyltransferase involved in mannoprotein biosynthesis. J. Biol. Chem. 279, 17921-17931

Lowe, J. B., and Marth, J. D. (2003) A genetic approach to mammalian glycan function. Annu. ReV. Biochem. 72, 643-691.

Marcus, S. L., Polakowski, R., Seto, N. O. L., Leinala, E., Borisova, S., Blancher, A., Roubinet, F., Evans, S. V., and Palcic, M. M. (2003) A single point mutation reverses the donor specificity of human blood group B-synthesizing galactosyltransferase. J. Biol. Chem. 278, 12403-12405.

Morera, S. et al. (1999) T4 phage b-glucosyltransferase: substrate binding and proposed catalytic mechanism. J. Mol. Biol. 292, 717-730.

Mulichak, A. M. et al. (2001) Structure of the UDP-glucosyltransferase GtfB that modifies the heptapeptide aglycone in the biosynthesis of vancomycin group antibiotics. Structure 9, 547-557.

Negishi, M. et al. (2003) Glucosaminylglycan biosynthesis: what we can learn from the X-ray crystal structures of glycosyltransferases GlcAT1 and EXTL2. Biochem. Biophys. Res. Commun. 303, 393-398.

Powell, J. T., and Brew, K. (1976) Metal ion activation of galactosyltransferase, J. Biol. Chem. 251, 3645-3652.

Pedersen, L. C., Darden, T. A., and Negishi, M. (2002) Crystal structure of beta 1,3 glucuronyltransferase I in complex with active donor substrate UDP-GlcUA. J. Biol. Chem. 277, 21869-21873.

Powell, J. T., and Brew, K. (1976) A comparison of the interactions of galactosyltransferase with a glycoprotein substrate (ovalbumin) and with R-lactalbumin, J. Biol. Chem. 251, 3653-3663.

Qasba, P. K., Ramakrishnan, B., and Boeggeman, E. (2005) Substrate-induced conformational changes in glycosyltransferases. Trends Biochem. Sci. 30, 53-62.

Ramakrishnan, B., Boeggeman, E, and Qasba P. K. (2004), Effect of the Met344His Mutation on the Conformational Dynamics of Bovine beta-1,4-Galactosyltransferase: Crystal Structure of the Met344His Mutant in Complex with Chitobiose. Biochemistry 2004, 43, 12513-12522.

Ramakrishnan, B., and Qasba, P. K. (2001) Crystal structure of lactose synthase reveals a large conformational change in its catalytic component, the beta1,4-galactosyltransferase-I, J. Mol. Biol. 310, 205-218.

Ramakrishnan, B., Shah, P. S., and Qasba, P. K. (2001a) R-Lactalbumin (LA) stimulates milk beta-1,4-galactosyltransferase I (beta4Gal-T1) to transfer glucose from UDP-glucose to N-acetylglucosamine. Crystal structure of beta4Gal-T1âLA complex with UDP-Glc, J. Biol. Chem. 276, 37665-37671.

Ramakrishnan, B., and Qasba, P. K. (2002) Structure-based design of beta1,4-galactosyltransferase I (beta4Gal-T1) with equally efficient N-acetylgalactosaminyltransferase activity: point mutation broadens beta4Gal-T1 donor specificity, J. Biol. Chem. 277, 20833-20839.

Ramakrishnan, B., Balaji, P. V., and Qasba, P. K. (2002a) Crystal structure of beta 1,4-galactosyltransferase complex with UDP-Gal reveals an oligosaccharide acceptor binding site, J. Mol. Biol. 318, 491-502.

Ramakrishnan, B., and Qasba, P. K. (2003) Comparison of the closed conformation of the beta1,4-galactosyltransferase-1 (beta4Gal-T1) in the presence and absence of R-lactalbumin (LA), J. Biomol. Struct. Dyn. 21, 1-8.

Ramakrishnan, B., Boeggeman, E., Ramasamy, V., and Qasba, P. K. (2004a) Structure and catalytic cycle of beta-1,4-galactosyltransferrase. Curr. Opin. Struct. Biol. 14, 593-600

Raman, R., Sasisekharan, V., and Sasisekharan, R. (2005) Structural insights into biological roles of protein-glycosaminoglycan interactions. Chem. Biol. 12, 267-277.

Ramasamy, V., Ramakrishnan, B., Boeggeman, E., and Qasba, P. K. (2003) The role of tryptophan 314 in the conformational changes of â1,4-galactosyltransferase-I, J. Mol. Biol. 331, 1065-1076.

Takase, K., and Ebner, K. E. (1984) Interaction of galactosyltransferase with R-lactalbumin and substrates, Curr. Top. Cell Regul. 24, 51-62.

Unligil, U. M. and Rini, J. M. (2000) Glycosyltransferase structure and mechanism. Curr. Opin. Struct. Biol. 10, 510-517.

---

What is claimed is:

1. An isolated polypeptide fragment of a beta (1,4)-galactosyltransferase I that retains the ability to transfer GalNAc or galactose from a sugar donor to a sugar acceptor, wherein the polypeptide fragment comprises SEQ ID NO: 2.

2. An isolated polypeptide fragment from a beta (1,4)-galactosyltransferase I that catalyzes the formation of a GalNAc-beta (1,4)-N-acetylgalactosamine bond in the presence of magnesium, wherein the polypeptide fragment comprises SEQ ID NO: 2.

3. An isolated amino acid sequence corresponding to the polypeptide fragment of claim 2.

4. A method of making a glycoprotein comprising incubating a reaction mixture comprising the polypeptide fragment of claim 2 with a sugar donor and a sugar acceptor in the presence of magnesium;

or a method of making a glycoprotein comprising incubating a reaction mixture comprising the polypeptide fragment of claim 2 with a sugar donor and a sugar acceptor;

or a method of making a glycoprotein comprising incubating a reaction mixture comprising the polypeptide fragment of claim 2 with a sugar donor, wherein the sugar donor comprises a UDP-galactose, UDP-GalNAc, UDP-GalNAc analogue or a UDP-Gal analogue, and an N-acetylglucosamine sugar acceptor in the presence of magnesium.

5. A composition comprising the polypeptide fragment of claim 2.

6. A method of coupling an agent to a carrier protein comprising:

incubating a reaction mixture comprising the polypeptide fragment of claim 2 with a sugar donor, and a carrier protein, in the presence of magnesium.

7. A kit comprising packaging material and the polypeptide fragment of claim 2.

* * * * *

SEQUENCE LISTING

<160> NUMBER OF SEQ ID NOS: 8

<210> SEQ ID NO 1
<211> LENGTH: 819
<212> TYPE: DNA
<213> ORGANISM: Homo sapiens

<400> SEQUENCE: 1

```
ctgcccgcat gccctgagga gtccccgctg cttgtgggcc ccatgctgat tgagtttaac      60
atgcctgtgg acctggagct cgtggcaaag cagaacccaa atgtgaagat gggcggccgc     120
tatgccccca gggactgcgt ctctcctcac aaggtggcca tcatcattcc attccgcaac     180
cggcaggagc acctcaagta ctggctatat tatttgcacc cagtcctgca gcgccagcag     240
ctggactatg gcatctatgt tatcaaccag gcgggagaca ctatattcaa tcgtgctaag     300
ctcctcaatg ttggctttca agaagccttg aaggactatg actacacctg ctttgtgttt     360
agtgacgtgg acctcattcc aatgaatgac cataatgcgt acaggtgttt ttcacagcca     420
cggcacattt ccgttgcaat ggataagttt ggattcagcc taccttatgt tcagttgttt     480
```

```
ggaggtgtct ctgctctaag taaacaacag tttctaacca tcaatggatt tcctaataat    540
tattggggct ggggaggaga agatgatgac atttttaaca gattagtttt tagaggcatg    600
tctatatctc gcccaaatgc tgtggtcggg aggacgcgtc acatccgcca ctcgagagac    660
aagaaaaatg aacccaatcc tcagaggttt gaccgaattg cacacacaaa ggagacaatg    720
ctctctaatg gtttgaactc actcacctac caggtgctgg atgtacagag atacccattg    780
tatacccaaa tcacagtgga catcgggaca ccgagctag                           819

<210> SEQ ID NO 2
<211> LENGTH: 272
<212> TYPE: PRT
<213> ORGANISM: Homo sapiens

<400> SEQUENCE: 2

Leu Pro Ala Cys Pro Glu Glu Ser Pro Leu Val Gly Pro Met Leu
 1               5                  10                  15

Ile Glu Phe Asn Met Pro Val Asp Leu Glu Leu Val Ala Lys Gln Asn
                20                  25                  30

Pro Asn Val Lys Met Gly Gly Arg Tyr Ala Pro Arg Asp Cys Val Ser
            35                  40                  45

Pro His Lys Val Ala Ile Ile Ile Pro Phe Arg Asn Arg Gln Glu His
        50                  55                  60

Leu Lys Tyr Trp Leu Tyr Tyr Leu His Pro Val Leu Gln Arg Gln Gln
    65                  70                  75                  80

Leu Asp Tyr Gly Ile Tyr Val Ile Asn Gln Ala Gly Asp Thr Ile Phe
                85                  90                  95

Asn Arg Ala Lys Leu Leu Asn Val Gly Phe Gln Glu Ala Leu Lys Asp
            100                 105                 110

Tyr Asp Tyr Thr Cys Phe Val Phe Ser Asp Val Asp Leu Ile Pro Met
        115                 120                 125

Asn Asp His Asn Ala Tyr Arg Cys Phe Ser Gln Pro Arg His Ile Ser
    130                 135                 140

Val Ala Met Asp Lys Phe Gly Phe Ser Leu Pro Tyr Val Gln Leu Phe
145                 150                 155                 160

Gly Gly Val Ser Ala Leu Ser Lys Gln Gln Phe Leu Thr Ile Asn Gly
                165                 170                 175

Phe Pro Asn Asn Tyr Trp Gly Trp Gly Gly Glu Asp Asp Asp Ile Phe
            180                 185                 190

Asn Arg Leu Val Phe Arg Gly Met Ser Ile Ser Arg Pro Asn Ala Val
        195                 200                 205

Val Gly Arg Thr Arg His Ile Arg His Ser Arg Asp Lys Lys Asn Glu
    210                 215                 220

Pro Asn Pro Gln Arg Phe Asp Arg Ile Ala His Thr Lys Glu Thr Met
225                 230                 235                 240

Leu Ser Asn Gly Leu Asn Ser Leu Thr Tyr Gln Val Leu Asp Val Gln
                245                 250                 255

Arg Tyr Pro Leu Tyr Thr Gln Ile Thr Val Asp Ile Gly Thr Pro Ser
            260                 265                 270

<210> SEQ ID NO 3
<211> LENGTH: 415
<212> TYPE: PRT
<213> ORGANISM: Homo sapiens

<400> SEQUENCE: 3
```

```
Met Arg Leu Arg Glu Pro Leu Leu Ser Arg Ser Ala Ala Met Pro Gly
 1               5                   10                  15

Met Arg Phe Arg Glu Gln Phe Leu Gly Ser Ala Ala Met Pro Gly
             20                  25                  30

Ala Thr Leu Gln Arg Ala Cys Arg Leu Leu Val Ala Val Cys Ala Leu
                 35                  40                  45

His Leu Gly Val Thr Leu Val Tyr Tyr Leu Ser Gly Arg Asp Leu Ser
             50                  55                  60

Arg Leu Pro Gln Leu Val Gly Val Ser Ser Thr Leu Gln Gly Gly Thr
 65                  70                  75                  80

Asn Gly Ala Ala Ala Ser Lys Gln Pro Gly Glu Gln Arg Pro Arg
                     85                  90                  95

Gly Ala Arg Pro Pro Pro Leu Gly Val Ser Pro Lys Pro Arg Pro
                100                 105                 110

Gly Leu Asp Ser Ser Pro Gly Ala Ala Ser Gly Pro Gly Leu Lys Ser
                115                 120                 125

Asn Leu Ser Ser Leu Pro Val Pro Thr Thr Gly Leu Leu Ser Leu
    130                 135                 140

Pro Ala Cys Pro Glu Glu Ser Pro Leu Leu Val Gly Pro Met Leu Ile
145                 150                 155                 160

Asp Phe Asn Ile Ala Val Asp Leu Glu Leu Leu Ala Lys Lys Asn Pro
                165                 170                 175

Glu Ile Lys Thr Gly Gly Arg Tyr Ser Pro Lys Asp Cys Val Ser Pro
                180                 185                 190

His Lys Val Ala Ile Ile Pro Phe Arg Asn Arg Gln Glu His Leu
    195                 200                 205

Lys Tyr Trp Leu Tyr Tyr Leu His Pro Ile Leu Gln Arg Gln Gln Leu
210                 215                 220

Asp Tyr Gly Ile Tyr Val Ile Asn Gln Ala Gly Asp Thr Met Phe Asn
225                 230                 235                 240

Arg Ala Lys Leu Leu Asn Ile Gly Phe Gln Glu Ala Leu Lys Asp Tyr
                245                 250                 255

Asp Tyr Asn Cys Phe Val Phe Ser Asp Val Asp Leu Ile Pro Met Asp
                260                 265                 270

Asp Arg Asn Ala Tyr Arg Cys Phe Ser Gln Pro Arg His Ile Ser Val
                275                 280                 285

Ala Met Asp Lys Phe Gly Phe Ser Leu Pro Tyr Val Gln Tyr Phe Gly
                290                 295                 300

Gly Val Ser Ala Leu Ser Lys Gln Gln Pro Leu Ala Ile Asn Gly Phe
305                 310                 315                 320

Pro Asn Asn Tyr Trp Gly Trp Gly Gly Glu Asp Asp Ile Phe Asn
                325                 330                 335

Arg Leu Val His Lys Gly Met Ser Ile Ser Arg Pro Asn Ala Val Val
                340                 345                 350

Gly Arg Cys Arg Met Ile Arg His Ser Arg Asp Lys Lys Asn Glu Pro
                355                 360                 365

Asn Pro Gln Arg Phe Asp Arg Ile Ala His Thr Lys Glu Thr Met Arg
                370                 375                 380

Phe Asp Gly Leu Asn Ser Leu Thr Tyr Lys Val Leu Asp Val Gln Arg
385                 390                 395                 400

Tyr Pro Leu Tyr Thr Gln Ile Thr Val Asp Ile Gly Thr Pro Arg
                405                 410                 415
```

<210> SEQ ID NO 4

```
<211> LENGTH: 402
<212> TYPE: PRT
<213> ORGANISM: Bos sp.

<400> SEQUENCE: 4

Met Lys Phe Arg Glu Pro Leu Leu Gly Gly Ser Ala Ala Met Pro Gly
  1               5                  10                  15

Ala Ser Leu Gln Arg Ala Cys Arg Leu Leu Val Ala Val Cys Ala Leu
             20                  25                  30

His Leu Gly Val Thr Leu Val Tyr Tyr Leu Ala Gly Arg Asp Leu Arg
         35                  40                  45

Arg Leu Pro Gln Leu Val Gly Val His Pro Pro Leu Gln Gly Ser Ser
     50                  55                  60

His Gly Ala Ala Ala Ile Gly Gln Pro Ser Gly Glu Leu Arg Leu Arg
 65                  70                  75                  80

Gly Val Ala Pro Pro Pro Leu Gln Asn Ser Ser Lys Pro Arg Ala Arg
                 85                  90                  95

Arg Ala Pro Ser Asn Leu Asp Ala Tyr Ser His Pro Gly Pro Gly Pro
            100                 105                 110

Gly Pro Gly Ser Asn Leu Thr Ser Ala Pro Val Pro Ser Thr Thr Thr
        115                 120                 125

Arg Ser Leu Thr Ala Cys Pro Glu Glu Ser Pro Leu Leu Val Gly Pro
    130                 135                 140

Met Leu Ile Glu Phe Asn Ile Pro Val Asp Leu Lys Leu Ile Glu Gln
145                 150                 155                 160

Gln Asn Pro Lys Val Lys Leu Gly Gly Arg Tyr Thr Pro Met Asp Cys
                165                 170                 175

Ile Ser Pro His Lys Val Ala Ile Ile Ile Leu Phe Arg Asn Arg Gln
            180                 185                 190

Glu His Leu Lys Tyr Trp Leu Tyr Tyr Leu His Pro Met Val Gln Arg
        195                 200                 205

Gln Gln Leu Asp Tyr Gly Ile Tyr Val Ile Asn Gln Ala Gly Glu Ser
    210                 215                 220

Met Phe Asn Arg Ala Lys Leu Leu Asn Val Gly Phe Lys Glu Ala Leu
225                 230                 235                 240

Lys Asp Tyr Asp Tyr Asn Cys Phe Val Phe Ser Asp Val Asp Leu Ile
                245                 250                 255

Pro Met Asn Asp His Asn Thr Tyr Arg Cys Phe Ser Gln Pro Arg His
            260                 265                 270

Ile Ser Val Ala Met Asp Lys Phe Gly Phe Ser Leu Pro Tyr Val Gln
        275                 280                 285

Tyr Phe Gly Gly Val Ser Ala Leu Ser Lys Gln Gln Phe Leu Ser Ile
    290                 295                 300

Asn Gly Phe Pro Asn Asn Tyr Trp Gly Trp Gly Gly Glu Asp Asp Asp
305                 310                 315                 320

Ile Tyr Asn Arg Leu Ala Phe Arg Gly Met Ser Val Ser Arg Pro Asn
                325                 330                 335

Ala Val Ile Gly Lys Cys Arg Met Ile Arg His Ser Arg Asp Lys Lys
            340                 345                 350

Asn Glu Pro Asn Pro Gln Arg Phe Asp Arg Ile Ala His Thr Lys Glu
        355                 360                 365

Thr Met Leu Ser Asp Gly Leu Asn Ser Leu Thr Tyr Met Val Leu Glu
    370                 375                 380

Val Gln Arg Tyr Pro Leu Tyr Thr Lys Ile Thr Val Asp Ile Gly Thr
385                 390                 395                 400
```

Pro Ser

<210> SEQ ID NO 5
<211> LENGTH: 2013
<212> TYPE: DNA
<213> ORGANISM: Homo sapiens

<400> SEQUENCE: 5

| | | | | | | |
|---|---|---|---|---|---|---|
| ttggcctggc | ctgcttgtcg | ctgggatctg | aatgaccaaa | ccacttccca | ccatggctcc | 60 |
| tggaaggact | aaatgaagtc | atgagtataa | agtgctcctg | catggccagc | agccggatgc | 120 |
| ccgggcccac | tgggcgggcc | agtggccgcc | tgcgggatga | gcagactgct | ggggggggacg | 180 |
| ctggagcgcg | tctgcaaggc | tgtgctcctt | ctctgcctgc | tgcacttcct | cgtggccgtc | 240 |
| atcctctact | ttgacgtcta | cgcccagcac | ctggccttct | tcagccgctt | cagtgcccga | 300 |
| ggccctgccc | atgccctcca | cccagctgct | agcagcagca | gcagcagcag | caactgctcc | 360 |
| cggcccaacg | ccaccgcctc | tagctccggg | ctccctgagg | tccccagtgc | cctgcccggt | 420 |
| cccacggctc | ccacgctgcc | accctgtcct | gactcgccac | tggtcttgt | gggcagactg | 480 |
| ctgatcgagt | tcacctcacc | catgcccctg | agcgggtgc | agaggagaa | cccaggcgtg | 540 |
| ctcatgggcg | gccgatacac | accgcccgac | tgcaccccag | cccagacggt | ggcggtcatc | 600 |
| atccctttta | gacaccggga | acaccacctg | cgctactggc | tccactatct | acaccccatc | 660 |
| ttgaggcggc | agcggctgcg | ctacggcgtc | tatgtcatca | ccagcatgg | tgaggacacc | 720 |
| ttcaaccggg | ccaagctgct | taacgtgggc | ttcctagagg | cgctgaagga | ggatgccgcc | 780 |
| tatgactgct | tcatcttcag | cgatgtggac | ctggtcccca | tggatgaccg | caacctatac | 840 |
| cgctgcggcg | accaacccg | ccactttgcc | attgccatgg | acaagtttgg | cttccggctt | 900 |
| ccctatgctg | gctactttgg | aggtgtgtca | ggcctgagta | aggctcagtt | tctgagaatc | 960 |
| aatggcttcc | ccaatgagta | ctggggctgg | ggtggcgagg | atgatgacat | cttcaaccgg | 1020 |
| atctccctga | ctgggatgaa | gatctcacgc | ccagacatcc | gaatcggccg | ctaccgcatg | 1080 |
| atcaagcacg | accgcgacaa | gcataacgaa | cctaaccctc | agaggtttac | caagattcaa | 1140 |
| aacacgaagc | tgaccatgaa | gcgggacggc | attgggtcag | tgcggtacca | ggtcttggag | 1200 |
| gtgtctcggc | aaccactctt | caccaatatc | acagtggaca | ttgggcggcc | tccgtcgtgg | 1260 |
| cccctcggg | gctgacacta | atggacagag | gctctcggtg | ccgaagattg | cctgccagag | 1320 |
| gactgaccac | agcctggctg | gcagctgctc | tgtggaggac | ctccaggact | gagactgggc | 1380 |
| tctgttttcc | aagggtcttc | actaggcccc | ctagctacac | ctggaagttt | cagaacccac | 1440 |
| tttgggggc | ctcctgcctg | ggcaggctct | tcaagtgtgg | ccctctttgg | agtcaaccct | 1500 |
| ccttcccgac | cccctccccc | tagcccagcc | ccagtcactg | tcagggtcgg | gccagcccct | 1560 |
| gcactgcctc | gcagagtggc | ctgggctagg | tcactccacc | tctctgtgcc | tcagtttccc | 1620 |
| cccttgagt | cccctagggc | ctggaagggt | gggaggtatg | tctaggggc | agtgtctctt | 1680 |
| ccagggggaa | ttctcagctc | ttgggaaccc | ccttgctccc | agggagggg | aaacctttt | 1740 |
| cattcaacat | tgtaggggc | aagctttggt | gcgcccctg | ctgaggagca | gcccaggag | 1800 |
| gggaccagag | gggatgctgt | gtcgctgcct | gggatcttgg | ggttggcctt | tgcatgggag | 1860 |
| gcaggtgggg | cttggatcag | taagtctggt | tcccgcctcc | ctgtctgaga | gaggaggcag | 1920 |
| gagccccagg | gccggcttgt | gtttgtacat | tgcacagaaa | cttgtgtggg | tgctttagta | 1980 |
| aaaaacgtga | atggaaaaaa | aaaaaaaaaa | aaa | | | 2013 |

```
<210> SEQ ID NO 6
<211> LENGTH: 372
<212> TYPE: PRT
<213> ORGANISM: Homo sapiens

<400> SEQUENCE: 6

Met Ser Arg Leu Leu Gly Gly Thr Leu Glu Arg Val Cys Lys Ala Val
1               5                   10                  15

Leu Leu Leu Cys Leu Leu His Phe Leu Ala Val Ile Leu Tyr Phe
            20                  25                  30

Asp Val Tyr Ala Gln His Leu Ala Phe Phe Ser Arg Phe Ser Ala Arg
            35                  40                  45

Gly Pro Ala His Ala Leu His Pro Ala Ala Ser Ser Ser Ser Ser
        50                  55                  60

Ser Asn Cys Ser Arg Pro Asn Ala Thr Ala Ser Ser Gly Leu Pro
65                  70                  75                  80

Glu Val Pro Ser Ala Leu Pro Gly Pro Thr Ala Pro Thr Leu Pro Pro
                85                  90                  95

Cys Pro Asp Ser Pro Pro Gly Leu Val Gly Arg Leu Leu Ile Glu Phe
            100                 105                 110

Thr Ser Pro Met Pro Leu Glu Arg Val Gln Arg Glu Asn Pro Gly Val
            115                 120                 125

Leu Met Gly Gly Arg Tyr Thr Pro Pro Asp Cys Thr Pro Ala Gln Thr
130                 135                 140

Val Ala Val Ile Ile Pro Phe Arg His Arg Glu His His Leu Arg Tyr
145                 150                 155                 160

Trp Leu His Tyr Leu His Pro Ile Leu Arg Arg Gln Arg Leu Arg Tyr
                165                 170                 175

Gly Val Tyr Val Ile Asn Gln His Gly Glu Asp Thr Phe Asn Arg Ala
            180                 185                 190

Lys Leu Leu Asn Val Gly Phe Leu Glu Ala Leu Lys Glu Asp Ala Ala
        195                 200                 205

Tyr Asp Cys Phe Ile Phe Ser Asp Val Asp Leu Val Pro Met Asp Asp
210                 215                 220

Arg Asn Leu Tyr Arg Cys Gly Asp Gln Pro Arg His Phe Ala Ile Ala
225                 230                 235                 240

Met Asp Lys Phe Gly Phe Arg Leu Pro Tyr Ala Gly Tyr Phe Gly Gly
                245                 250                 255

Val Ser Gly Leu Ser Lys Ala Gln Phe Leu Arg Ile Asn Gly Phe Pro
            260                 265                 270

Asn Glu Tyr Trp Gly Trp Gly Gly Glu Asp Asp Ile Phe Asn Arg
        275                 280                 285

Ile Ser Leu Thr Gly Met Lys Ile Ser Arg Pro Asp Ile Arg Ile Gly
290                 295                 300

Arg Tyr Arg Met Ile Lys His Asp Arg Asp Lys His Asn Glu Pro Asn
305                 310                 315                 320

Pro Gln Arg Phe Thr Lys Ile Gln Asn Thr Lys Leu Thr Met Lys Arg
                325                 330                 335

Asp Gly Ile Gly Ser Val Arg Tyr Gln Val Leu Glu Val Ser Arg Gln
            340                 345                 350

Pro Leu Phe Thr Asn Ile Thr Val Asp Ile Gly Arg Pro Pro Ser Trp
        355                 360                 365

Pro Pro Arg Gly
    370
```

```
<210> SEQ ID NO 7
<211> LENGTH: 4
<212> TYPE: PRT
<213> ORGANISM: Homo sapiens
<220> FEATURE:
<221> NAME/KEY: MOD_RES
<222> LOCATION: (1)
<223> OTHER INFORMATION: Arg-[GlcNAcbeta1,2-Manalpha1,6-
      (GlcNAcbeta1,2-Manalpha1,3)-Manbeta1,4-GlcNAcbeta1,4-GlcNAcbeta]

<400> SEQUENCE: 7

Arg Asn Glu Gly
  1

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Pro Thr Thr Asp Ser Thr Thr Pro Ala Pro Thr Thr Lys
  1               5                  10
```